United States Patent [19]

Kurtz et al.

[11] 4,231,354
[45] Nov. 4, 1980

[54] PULSATILE BLOOD PUMPING APPARATUS AND METHOD

[75] Inventors: Robert J. Kurtz, Cliffside Park, N.J.; Spencer J. Silverstein, Ithaca, N.Y.

[73] Assignee: Howmedica, Incorporated, New York, N.Y.

[21] Appl. No.: 924,567

[22] Filed: Jul. 14, 1978

[51] Int. Cl.³ .......................... A61M 1/03; A61F 1/24
[52] U.S. Cl. .............................. 128/1 D; 128/214 R; 3/1.7
[58] Field of Search ................. 128/1 D, 1 R, 214 R; 3/1.7

[56] References Cited

U.S. PATENT DOCUMENTS

| | | | |
|---|---|---|---|
| 3,421,497 | 1/1969 | Chesnut et al. | 128/1 |
| 3,426,743 | 2/1969 | Chesnut et al. | 128/1 |
| 3,592,183 | 7/1971 | Watkins et al. | 128/1 D X |
| 3,860,968 | 1/1975 | Shapiro | 3/1 |
| 3,878,567 | 4/1975 | Purdy | 3/1.7 |
| 3,966,358 | 6/1976 | Heimes et al. | 128/1 D X |
| 4,016,871 | 4/1977 | Schiff | 3/1.7 X |

OTHER PUBLICATIONS

Landis, D. L. et al., *Trans. Am. Soc. Artif. Intern. Organs.*, vol. XXII, pp. 519–525, 1977.
Hiller, K. W. et al., *Amer. Journ. of Med. Electronics*, 1963, Jul.–Sep., pp. 212–221.
Kirby, C. K. et al., *Surgery*, Oct. 1964, vol. 56, No. 4, pp. 719–725.
Lindgren, N., *IEEE Spectrum*, Sep. 1965, vol. 2, No. 9.

Primary Examiner—Kyle L. Howell
Attorney, Agent, or Firm—Cushman, Darby & Cushman

[57] ABSTRACT

An intracorporeal, extracorporeal, cardiac assist, perfusion device or other pulsatile blood pumping system for circulating blood within living tissue under automatic control. Plural physiologic parameters of the tissue are monitored and utilized to control plural operating parameters of the pump during succeeding cycles of its operation so as to restore the monitored physiologic parameters to desired predetermined (but adjustable) values.

24 Claims, 37 Drawing Figures

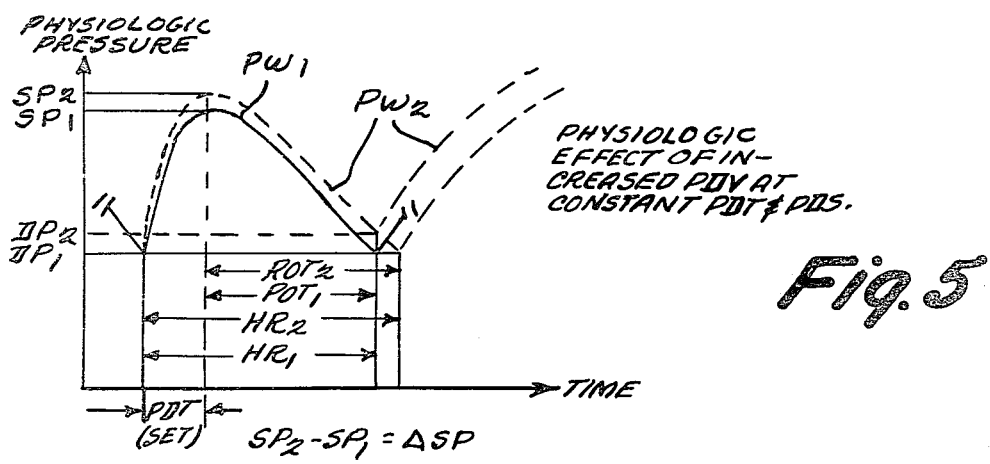
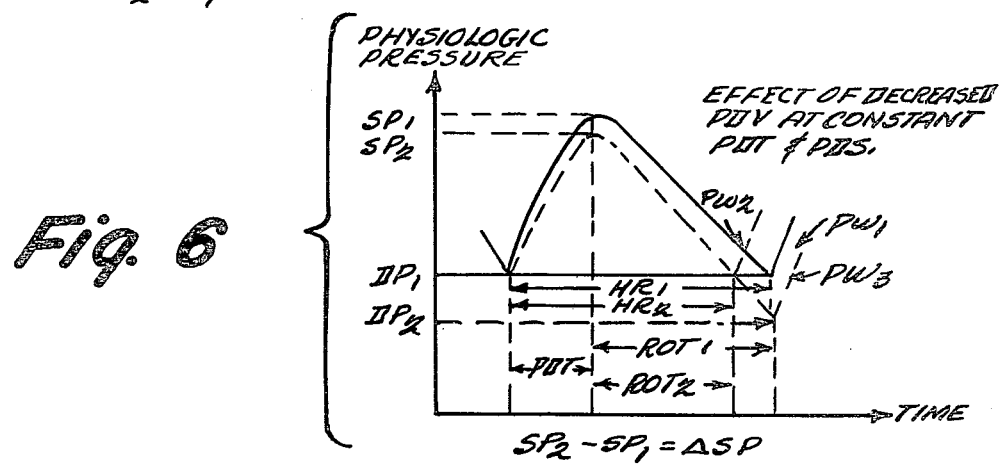
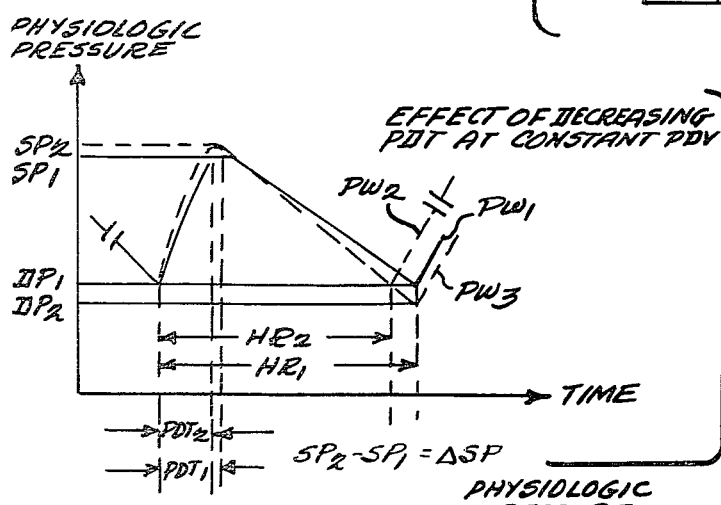
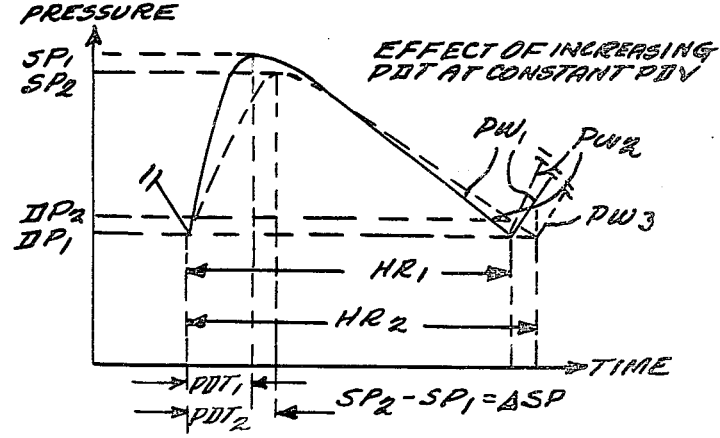

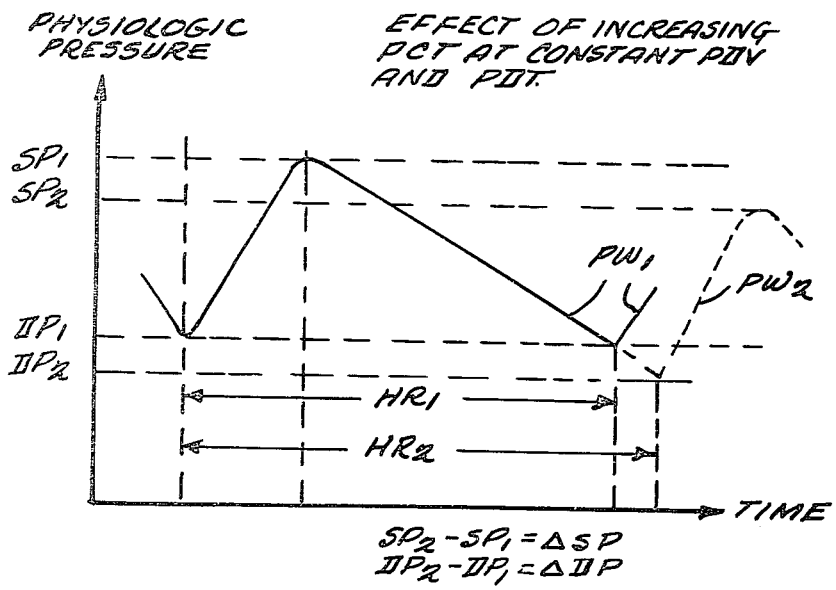
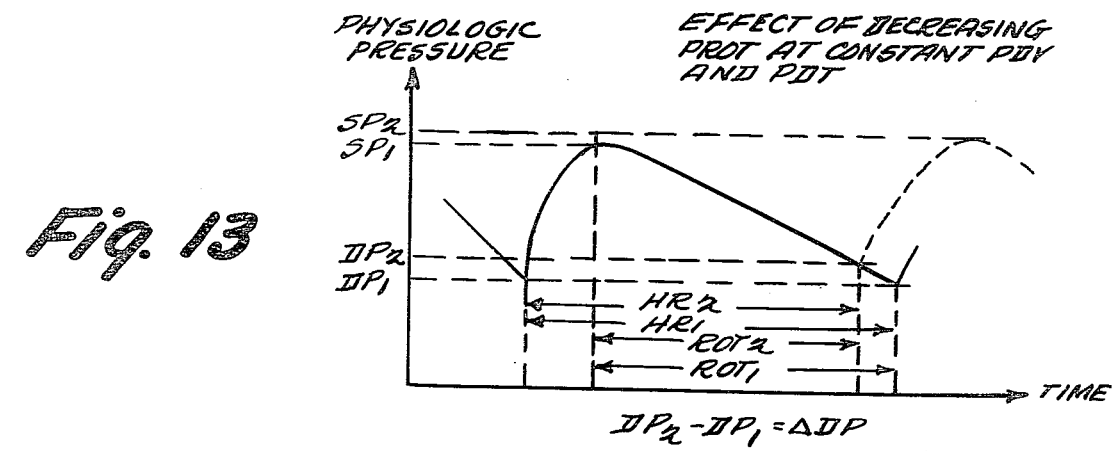
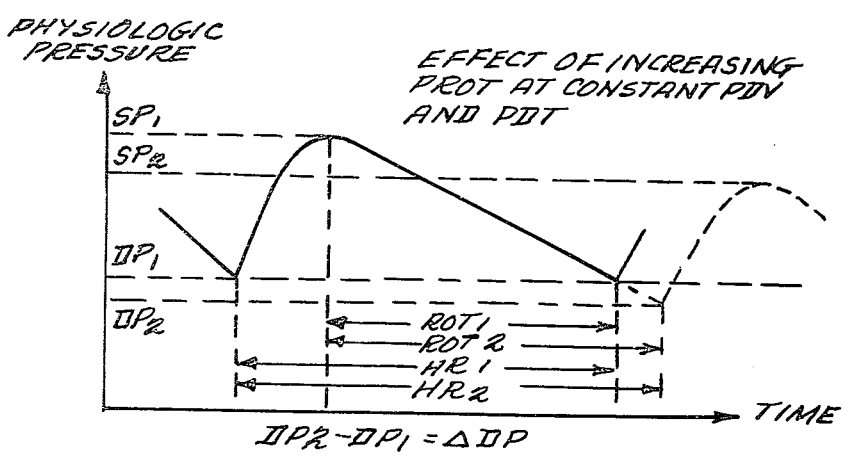

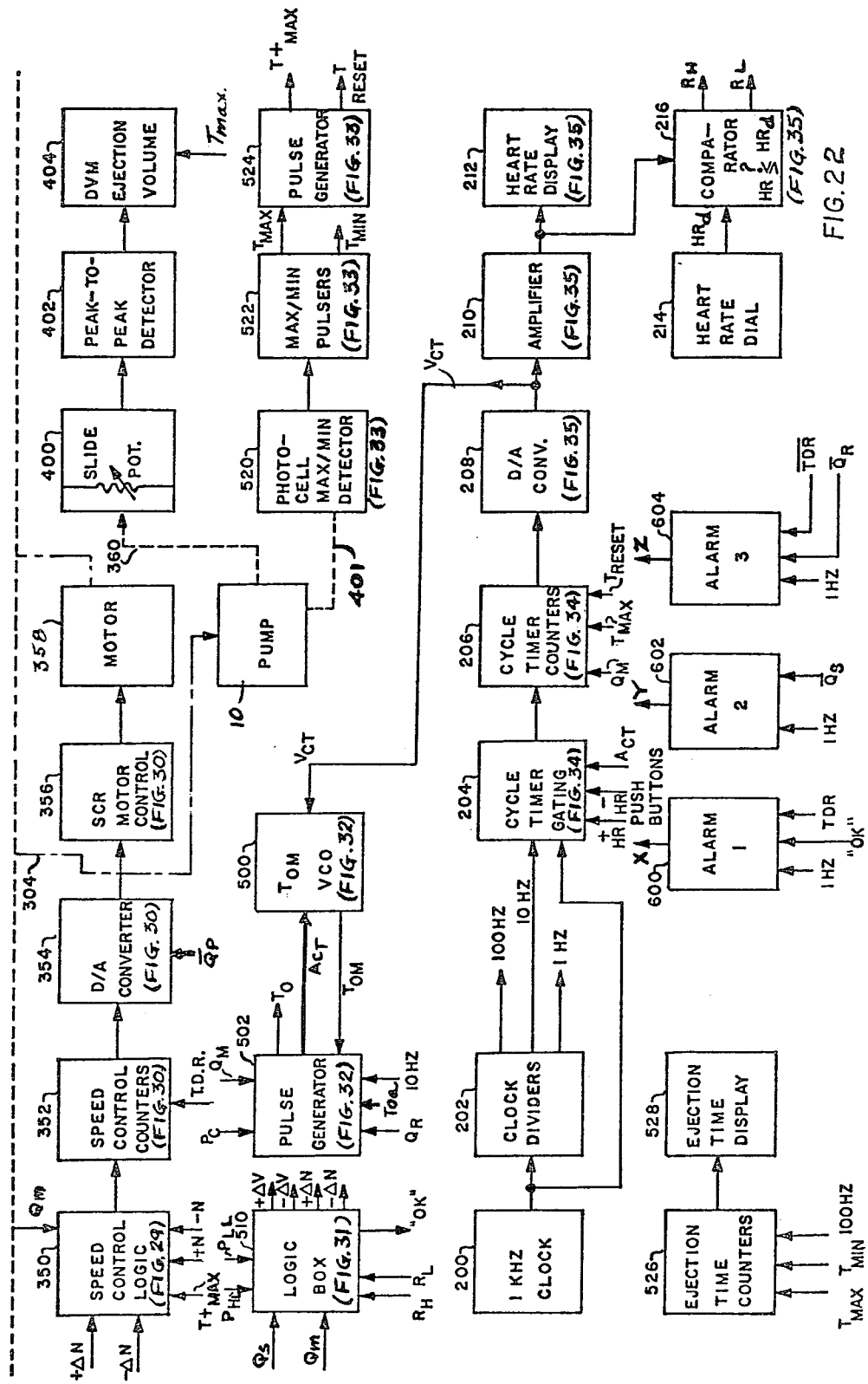

PULSATILE BLOOD PUMPING APPARATUS AND METHOD

This invention relates generally to a class of blood pumping systems suitable for use as an implantable or extracorporeal pumping system or as a cardiac assist or perfusion device. In particular, it relates to a pulsatile blood pumping system which is greatly superior to the conventional roller-type of blood pump because the new system maintains the desired condition of a living patient or organ.

A closed loop feedback circuit is employed to monitor plural physiologic parameters of the system and to control the pulsatile pump so as to automatically maintain these parameters at desired preset values. For a given patient or organ, the desired values for plural physiologic parameters are determined by a qualified person. Such desired values are then manually input to the system which thereafter automatically operates to maintain the actual parameter values.

The physiologic system within living tissue is constantly changing. Metabolic demands, vascular resistance, and compliance, the state of hydration, as well as other factors which can change with time, make the proper control of a pulsatile blood pump an especially critical matter. For example, the vascular compliance is nonlinear. Therefore a rather small excess volume of blood delivered at a time when the input is near its elastic limit can raise the blood pressure to disastrous levels resulting in a rupture of a blood vessel or the like. Although the more commonly used roller-type pump is easier to control in many respects, there is a need for a pulsatile pump system which many feel provides superior physiologic effects. Of course, as just noted, control of such a pulsatile system can be the critical and limiting factor in its use.

At present two types of pulsatile pumps commercially available are the Bentley pump and the Harvard pump. One uses a pneumatically operated system and the other uses a mechanically operated piston pump. However, both are open loop systems which repetitiously provide preset pump operating parameters without regard to the changing effect thereby produced on the living tissue involved. Presumably an operator is supposed to manually monitor the patient and keep readjusting the preset pump parameters during pump operation.

Other pulsatile pump systems have also been described in prior U.S. Pat. Nos. 3,426,743-Chestnut; 3,421,497-Chestnut; 3,592,183-Watkins; and 3,878,567-Purdy. However, all these prior approaches have failed to provide a comprehensive system which adequately and simultaneously controls a whole set of necessary physiologic parameters so as to become a truly automatic pump system which successfully mimics the natural human heart's pumping functions.

For example, both Chestnut '743 and '497 disclose a pulsatile pump system with the pump repetition rate controlled by the measured heart rate. Although the pump stroke is also decreased (thus decreasing the volume of blood delivered each cycle) as the heart rate increases, this control is really based on only one physiologic parameter—namely heart rate. In fact, in Chestnut '497 the actual pump operation is triggered a preset time delay after a predetermined point in an EKG signal. This manual adjustment is apparently critical and appears to be a continuing manual requirement during pump operations. In view of the uncontrolled blood system nonlinearities, etc., there may be unacceptable and uncontrolled changes in other important physiologic parameters (e.g., systolic and diastolic blood pressures).

Watkins '183 is apparently also a totally open loop system except for the repetition rate which may be triggered by a selected portion of an EKG signal and this synchronized with the patient's heart. Purdy '567 discloses an artificial heart where average blood pressure is monitored to control both the pumping stroke and rate. Here the stroke and rate are both apparently increased in response to increased average blood pressure. There may be other such prior pulsatile systems as well. However, in all cases, it is believed that only a single physiologic parameter is used as the controlling factor in pump operation.

Now, however, it has been discovered that improved overall system operation results from using plural measured physiologic parameters to control a pulsatile pump so as to simultaneously maintain these plural parameters at desired preset levels. An automatic closed loop pump control based on predetermined logic functions of the monitored interrelated plural parameters permits the system of this invention to converge upon a full range of preset physiologic parameters.

In the presently preferred embodiment of this invention the physiologic parameters of systolic blood pressure (SP), diastolic blood pressure (DP) and heart rate (HR) (or heart period $HP=1/HR$) or other related parameters are simultaneously maintained at preset values by independent and automatic control of pump delivery speed (PDS), pump delivery volume (PDV) and pump cycle time (PCT) or related pump operating parameters. The type of closed loop logic feedback control used provides for the first time automatic accurate mimicking of the heart function so as to permit true replacement of the heart function by a machine. For example, in cases of fight or flight, a different set of physiologic parameters may be selected. Thus, when certain conditions are detected, it may be desirable to change the set of control and controlled parameters and/or the logic functions used in effecting such control.

These and other objects and advantages of this invention will be better appreciated by reading the following detailed description taken in conjunction with the accompanying drawings, of which:

FIGS. 3-20 are graphs of blood pressure and pump delivery rates depicting relative physiologic and pump parameters for differing operating conditions;

Figure 23:
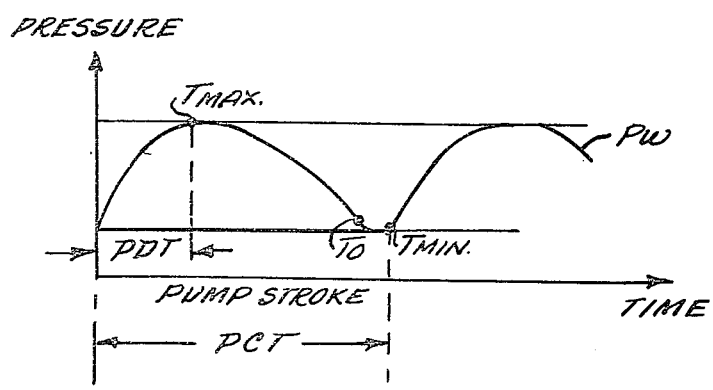
Figure 21:
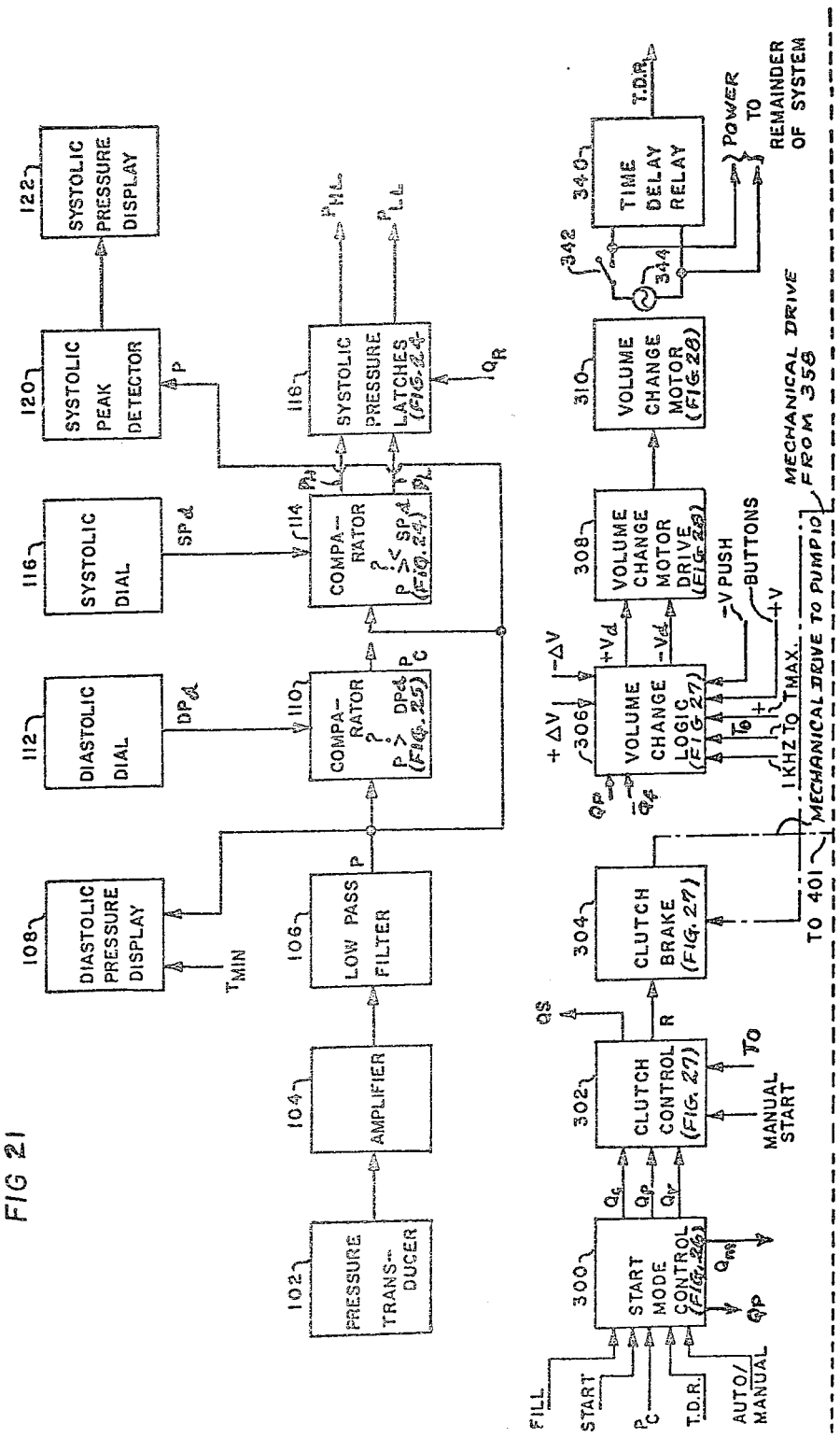

FIGS. 21-22 together constitute a block diagram of an exemplary embodiment of electronic circuits arranged according to this invention;

FIG. 23 is a blood pressure waveform showing the relative timing of certain control signals generated in the system of FIGS. 21-22; and FIGS. 24-35 are detailed schematic diagrams of certain functional blocks shown in FIGS. 21-22.

Figure 1:
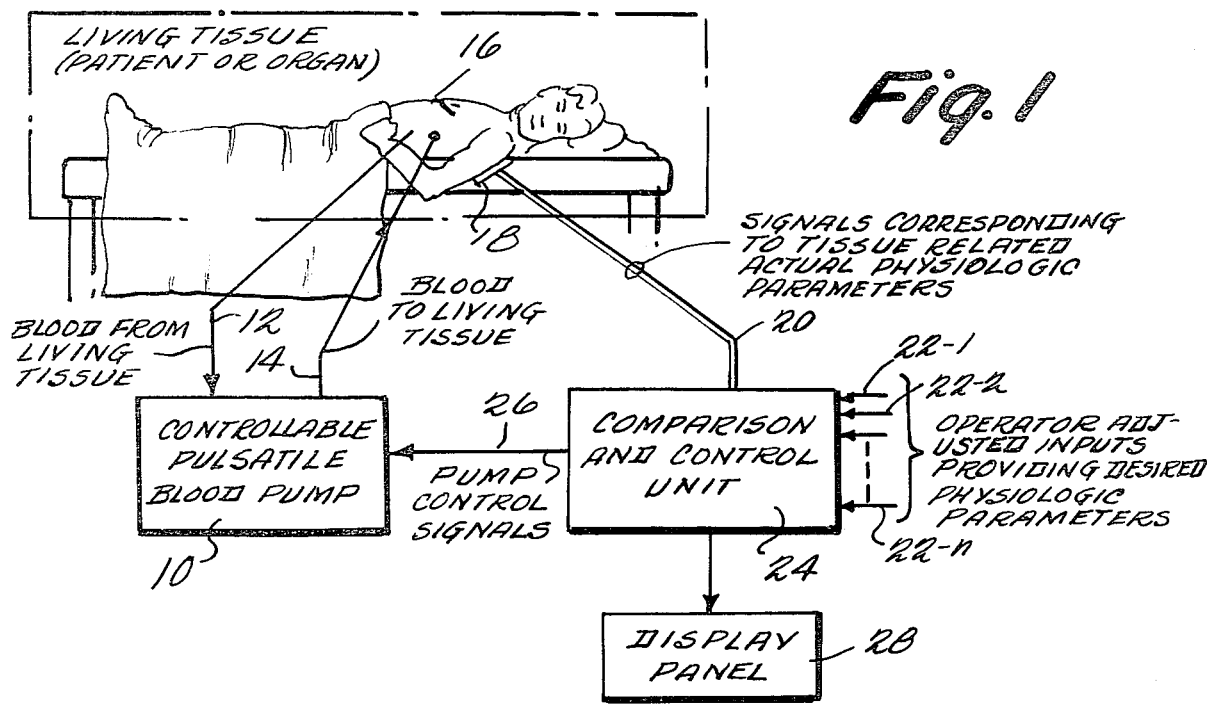
FIG. 1 is a general block diagram of the pumping system of this invention.

The closed loop feedback controlled pumping system of this invention is generally shown in FIG. 1. A controllable pulsatile blood pump 10 is conventionally connected via conduits 12 and 14 to circulate blood or to assist in such circulation within a human patient 16. If an organ is to be perfused, a blood-like substance such as plasma may be circulated.

Plural physiologic parameters are conventionally sensed by one or more sensors 18 physically associated with the patient 16 to produce a corresponding plurality of electrical signals on the conductors of cable 20 representing these parameters. As will be appreciated, the sensor 18 may provide one complex electrical signal (e.g., representing a blood pressure wave, cardiac output, cardiac ejection time, metabolic demands, oxygen consumption, cardiac work function, etc.) which is later processed to provide the plural electrical signals each corresponding to one of the actual physiologic parameters being monitored. Alternatively, separate sensors may be provided for each physiologic parameter. As will also be appreciated, these sensors will be conventionally affixed to the patient as desired. The FIG. 1 showing of a single sensor affixed to the patient's arm is a purely schematic depiction.

Desired values for plural physiologic parameters are then preset on inputs 22-1, 22-2, ... 22-n by a qualified operator. Depending upon the specific application, certain feedback or measured parameters are allowed to "float" to any reasonable value. Desired parameters may also be held "constant," or they may be assigned "goal" values. The choice of parameters allowed to "float" and to be held "constant" must permit the system to converge on the predetermined desired "goal" values. While such choices may differ for different applications, the "goal" and "constant" parameters must be selected so as to be non-restrictive with respect to each other. In the presently preferred embodiment, the physiologic parameters of "systolic pressure" (SP), and "heart rate" (HR) are used as "goal" parameters while "diastolic pressure" (DP) is held constant.

Once the "goal", "float" and "constant" parameters and values are chosen, they are preset into the system via inputs 22-1, 22-2, ... 22-n by an operator. This preset selection will also result in activation of appropriate circuitry in the control unit 24 to effect the necessary closed loop feedback control signals to the pump 10 via cable 26. For any given configuration of "goal", "float" and "constant" parameters, a specific set of logical rules is employed to generate the pump control signals on cable 26. Of course, if the pump system is manufactured for only a single application, the control unit may be conditioned at the factory to perform only according to one suitable set of logical rules.

Although the exemplary embodiment of the pumping system to be described in detail achieves such logical control through hard-wired electrical circuits, it will be appreciated that fully equivalent control could be achieved in part or altogether with a suitably programmed general purpose computer or controller. In fact, as mini and micro computer technology advances and as this invention is reduced to a commercial embodiment, such a programmed general purpose controller may become the preferred embodiment.

In operation, the system of FIG. 1 would be operated as follows:

Depending upon the physical characteristics of the patient or organ to be perfused, the operator dials in the desired values to be maintained. Actual values of physiologic parameters are then fed from the patient, organ, etc., to both the operator display panel 28 for patient monitoring, and to the comparison and control circuit module 24. The feedback signals are then compared to the desired values set by the operator, and then a set of control signals is generated which are sent to control the pump 10. The pump unit 10, governed by the pump control unit 24, delivers fluid through the fluid circuitry to the patient or organ being perfused 16. Physiologic signals from the patient, organ, etc., are continuously fed to the operator display panel 28 and the comparison and control module 24, and the process continues automatically without the necessity of operator intervention. This is achieved by constantly monitoring the current physiologic state and effecting changes in the pumping unit 10 so that the actual physiologic parameters constantly converge on the preset dialed-in values. In this manner, a whole set of desired physiologic parameters can be maintained despite changing conditions in the patient, or organ being perfused.

Figure 2:
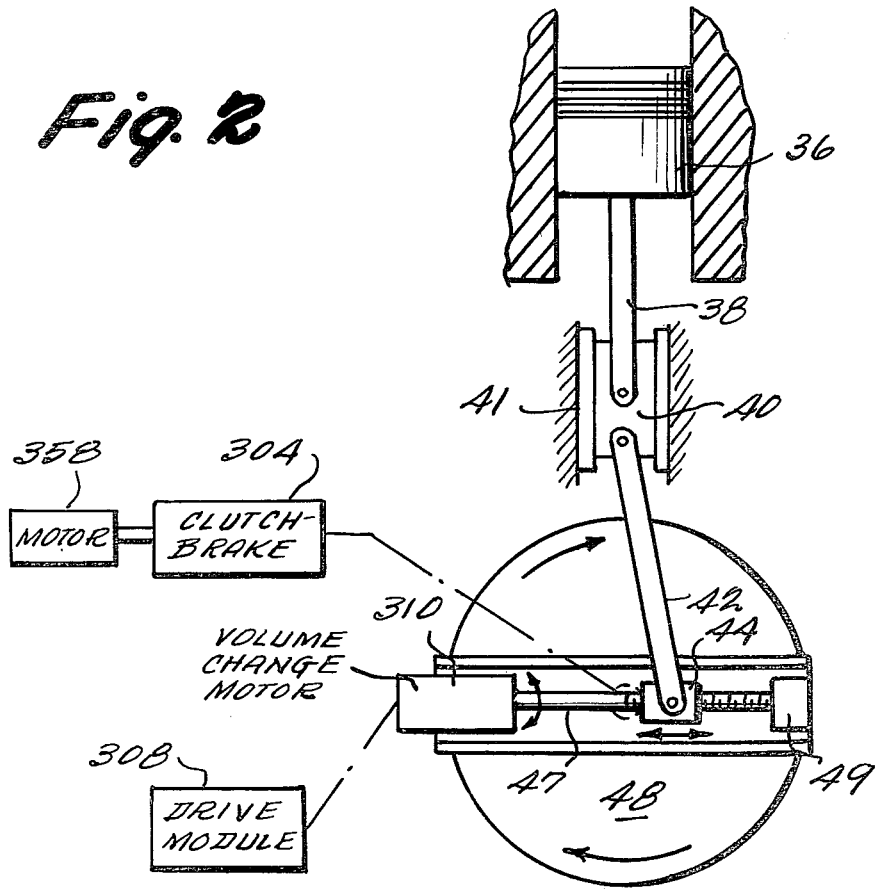
FIG. 2 is a schematic drawing of a pulsatile pump suitable for use with this invention.

The piston, cylinder, valves, and other features of pump 10 may generally be of conventional design. FIG. 2 illustrates a preferred linkage for varying the ejection volume of pump 10.

Referring to FIG. 2, piston 36 of pump 10 is pivotally mounted on a connecting rod 38. The other end of rod 38 is pivotally connected to a block 40 which is slidable in guides 41 diagrammatically shown. Also pivotably connected to block 40 is one end of a connecting rod 42, the other end of which is pivotally connected to a threaded block 44. Threaded block 44 is threaded onto a threaded shaft 47 having one end connected to the output shaft of volume change motor 310. Volume change motor 310 is fixedly mounted on a rotating drive wheel 48 which is conventionally connected through clutch-brake 304 to motor 358. Motor 310 is so mounted that shaft 47 is parallel to the plane of drive wheel 48. Shaft 47 is supported by a suitable support means 49 to prevent lateral movement of the shaft. Conventional electrical coupling means (not shown) connects volume change motor 310 to the output of drive module 308. Operation of motor 310 results in the displacement of slide 44 along shaft 47, the direction of the displacement being determined by the direction in which motor 310 is caused to rotate by drive module 308. When pump motor 358 is actuated, wheel 48 will be rotated to cause reciprocating movement of pump piston 36 through linkage 38, 40, 42 and threaded block 44. The length of stroke of piston 36 is determined by the position of block 44 on drive wheel 48. When a maximum stroke length is required for piston 36, block 44 will be driven by volume change motor 310 to a position adjacent the periphery of wheel 48. A minimum stroke for pump piston 36 will be provided when block 44 is disposed near the center of wheel 48.

Figure 3:
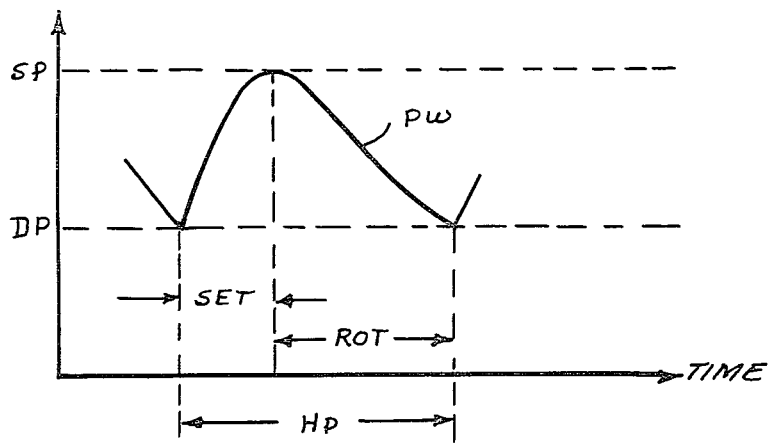

Referring to FIG. 3, there is shown an idealized typical pulsatile blood pressure wave, PW. Wave PW has successive peaks called systolic pressure, denoted as SP, and successive troughs called diastolic pressure, DP. The time between any two similar points on successive waves is referred to heart period (HP). Its reciprocal is heart rate (HR) . These are physiologic parameters.

In the preferred embodiment, the time between two successive SP peaks is used to measure HP. The HP is divided into two parts, the first part occurring from the DP trough to the SP peak. This first time is the systolic ejection time, denoted SET. The second portion occurring from an SP peak to a DP trough is referred to as runoff time, denoted as ROT.

Figure 4:
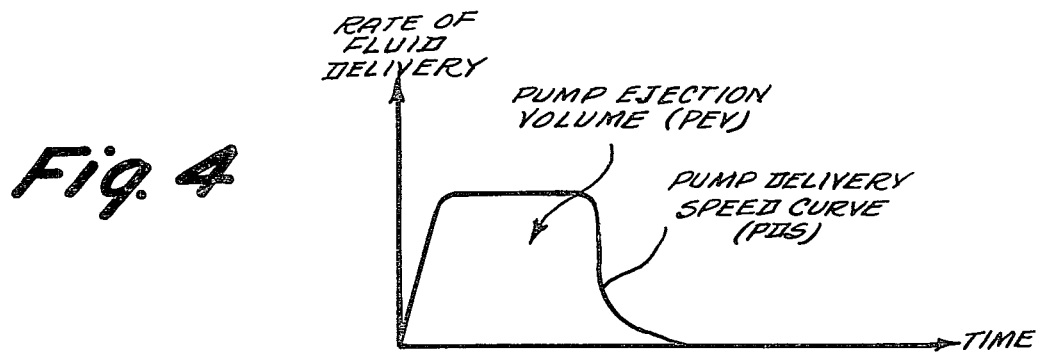

In describing the pump operating parameters, the volume of fluid delivered per stroke will be termed the "pump delivery volume", denoted PDV. A second pump parameter is the "pump delivery speed", denoted PDS. Its reciprocal is the "pump delivery time", denoted PDT. The time between two similar points on two successive pumping cycles is the "pump cycle time", denoted PCT. Its reciprocal is the "pump repetition rate", denoted PRR. Referring to FIG. 4, the area under the fluid rate delivery curve is the pump ejection volume, denoted PEV.

It is desirable to maintain the physiologic parameters SP, DP and HR as the normal heart would do. This invention allows for the first time, an extracorporeal, or intracorporeal cardiac assist, or perfusion device to do this. The system involves a controllable means for pumping a fluid, and in the preferred embodiment, blood into a patient's vascular system.

There are physiologic parameters which roughly correspond to some of the pump parameters. The physiologic systolic ejection volume SEV roughly corresponds to PDV. The physiologic parameter SET roughly corresponds to PDT. The physiologic parameter HR roughly corresponds to PRR, and finally HP corresponds roughly to PCT.

Figure 4A:
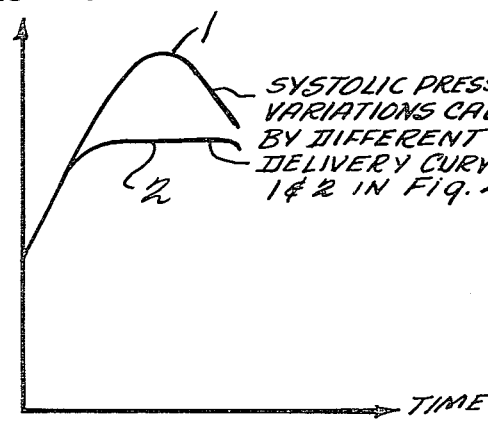
Figure 4B:
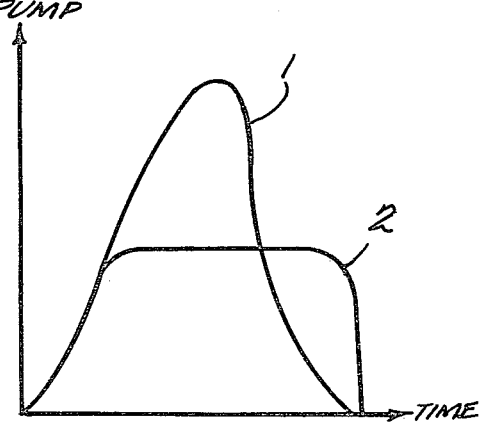

The correspondence of these parameters is not a one to one mapping. Variation, for example, in the pump delivery fluid curve at a constant PDT, will give different systolic pressures at the same PDV. This can be seen in FIGS. 4A and 4B.

The physiologic parameter of SET does not indicate what wave shape is desired, obtained or used. In some cases, where a short PDT is necessary, a ramp-type acceleration may be best, while at slower rates, a sinusoidal, cycloidal, or other arbitrary shape, might be desirable to minimize, for example, hemolysis.

The physiologic system is a constantly changing system. Metabolic demands, vascular resistance, and compliance in the state of hydration, as well as other factors which can change with time, necessitate the use of a closed loop feedback controlled system to maintain the desired physiologic parameters and in the preferred embodiment, these are SP, DP and HR.

FIG. 5 shows the effect of increasing PDV at a constant PDT and PDS curve. SP will increase by an amount ΔSP. This is because the vascular system in the preferred embodiment will have delivered to it, at the same PDT and PDS curve, a higher volume of fluid, and since the runoff characteristics of the vascular system are relatively unchanged, the physiologic pressure must be higher. There are now at least two possible alternatives to allow the initiation of the next cycle. If DP is to be held constant, then HP will increase (i.e., HR will decrease). If HR is to remain constant, then DP will increase.

Conversely, FIG. 6 shows the effect of decreasing PDV with a constant PDT. SP will decrease by an amount, ΔSP. There are now also at least two possible alternatives to initiate the next cycle. If DP is to be held constant, then HP will decrease (i.e., the HR will increase). If HR is to remain constant, then DP will increase.

FIG. 7 shows the effect of decreasing the PDT (e.g., increasing PDS) at a constant PDV. SP will increase by an amount ΔSP. This is because if the fluid is delivered at a faster rate, the pressure developed in the system to which it is delivered must be raised since the runoff characteristics are relatively slowly changing. Here there are also at least two possible alternatives to initiate the next cycle. If DP is to be held constant, then HP will decrease (i.e., HR will increase). If HR is to remain constant, DP will decrease.

Conversely, FIG. 8 shows the effect of increasing the PDT at a constant PDV. The SP will decrease by an amount ΔSP. There are at least two possible alternatives to initiate the next cycle. If DP is to be held constant, then HP will increase (i.e., HR will decrease). If HR is to remain constant, then DP will increase.

Figure 9:
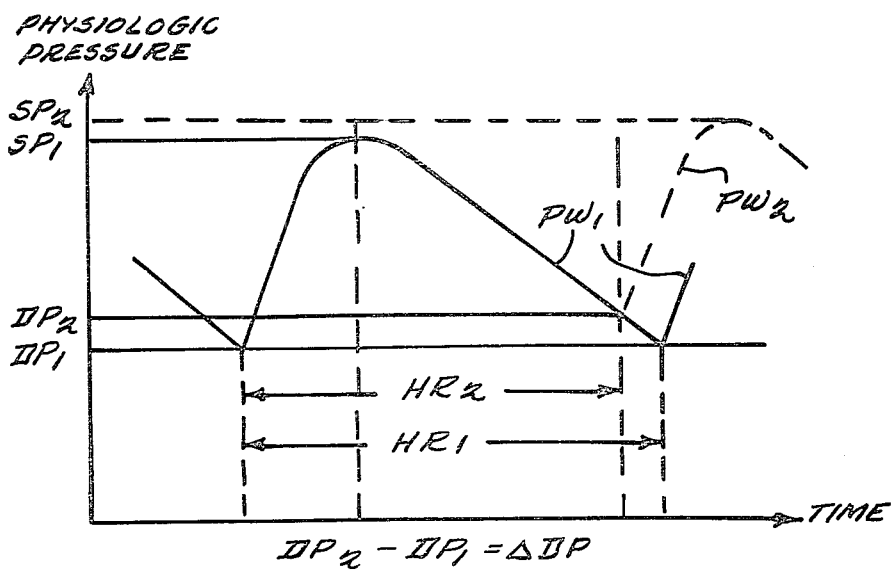

FIG. 9 shows the effect of increasing diastolic pressure at a constant PDT and PDV. SP will increase by an amount ΔSP in the next cycle. HP will decrease (i.e., the HR will increase).

Figure 10:
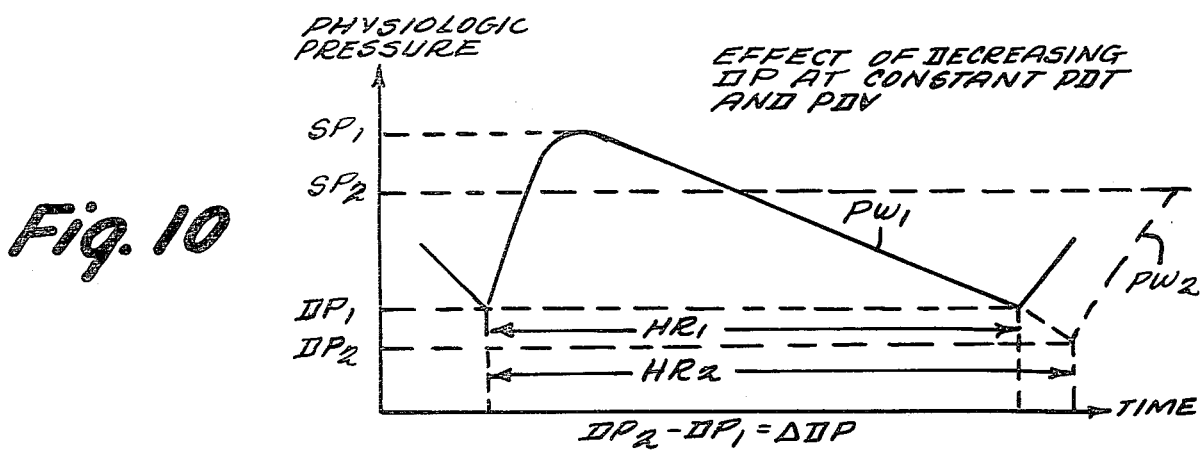

FIG. 10 shows the effect of decreasing diastolic pressure at a constant PDT and PDV. SP will decrease by an amount ΔSP in the next cycle, and HP will increase (i.e., the HR will decrease).

Figure 11:
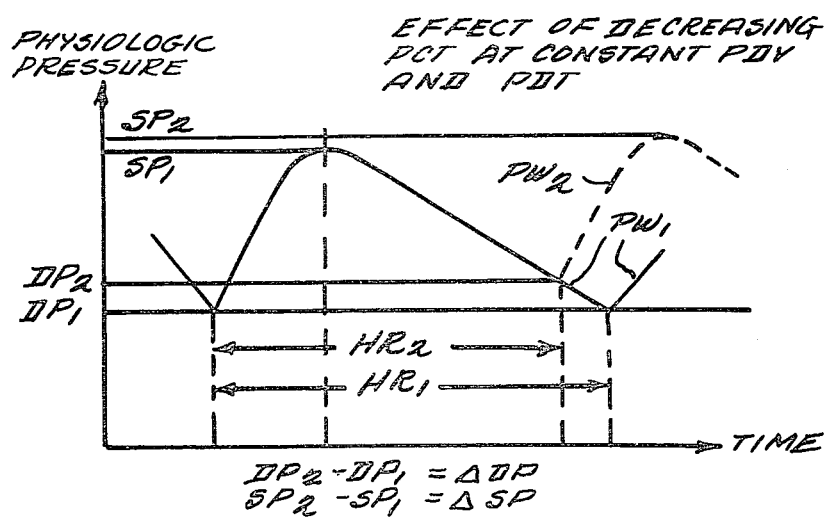

FIG. 11 shows the effect of decreasing PCT with a constant PDV and PDT. If PCT is to be shortened (i.e., the PRR is to increase), on the next stroke, SP will increase by an amount ΔSP. DP for the next stroke will also increase by an amount ΔDP.

FIG. 12 shows the converse situation of FIG. 11. If the PCT is increased during a stroke (i.e., the PRR is decreased), then the only parameter of this first stroke that would change would be DP, and it would decrease by an amount ΔDP. For the next strokes, SP would also decrease by an amount ΔSP.

FIG. 13 shows the effect of changing the pump runoff time (PROT) with PDV and PDT constant. If the PROT is decreased, then on the next stroke, SP will increase by an amount ΔSP. DP on the initial stroke will be increased by an amount ΔDP.

FIG. 14 shows the converse of FIG. 13. If PROT is increased with constant PDV and PDT, then SP on the next stroke would decrease by an amount ΔSP, and DP on the initial stroke would decrease by an amount ΔDP.

Figure 15:
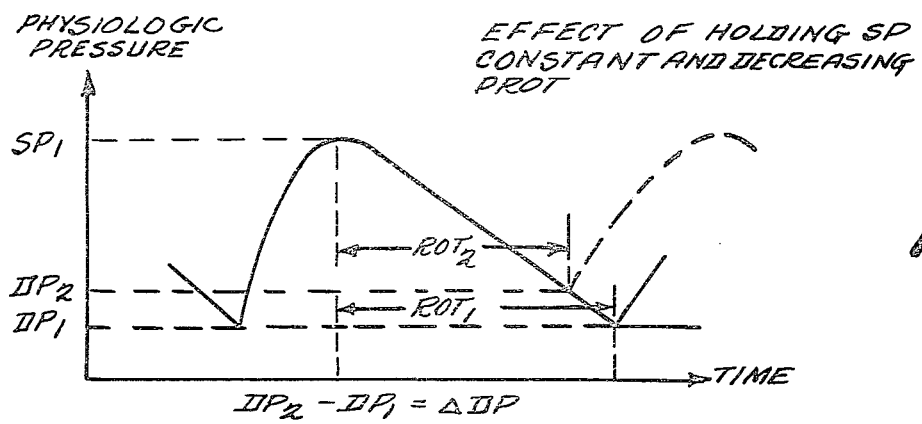

FIG. 15 shows the effect of holding SP constant. The next cycle can be initiated by the variable PROT. If the PROT is decreased then the PCT would decrease (e.g., the PRR would decrease).

Figure 16:
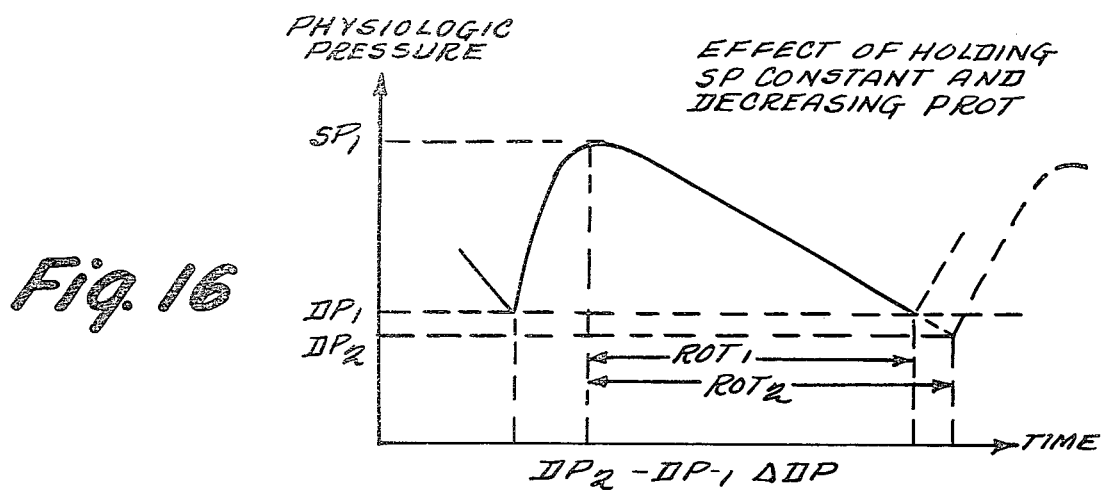

Conversely, FIG. 16 shows the effect of holding SP constant and increasing PROT. If PROT is increased, then PCT would increase (e.g., the PRR would decrease).

Figure 17:
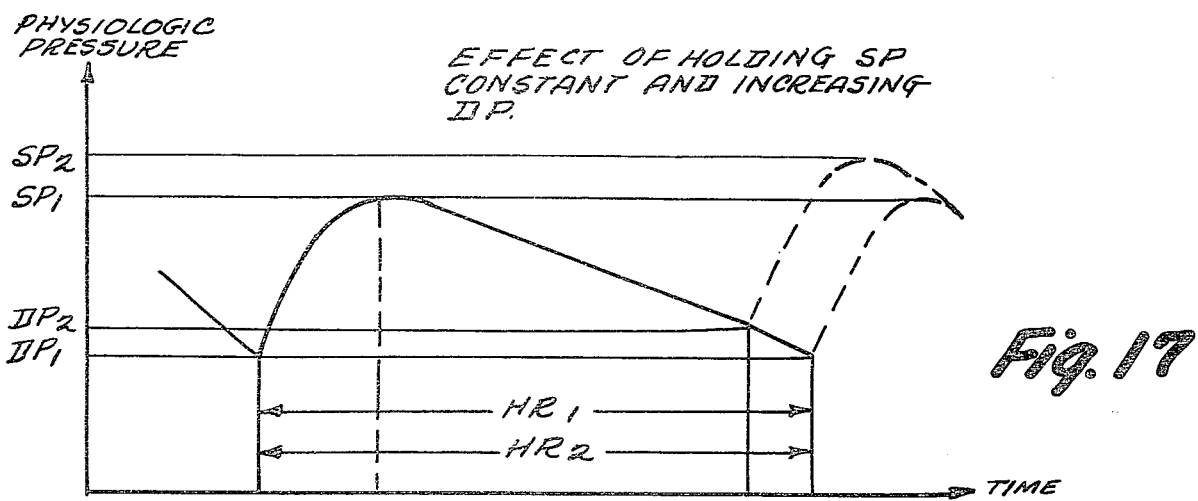
Figure 18:
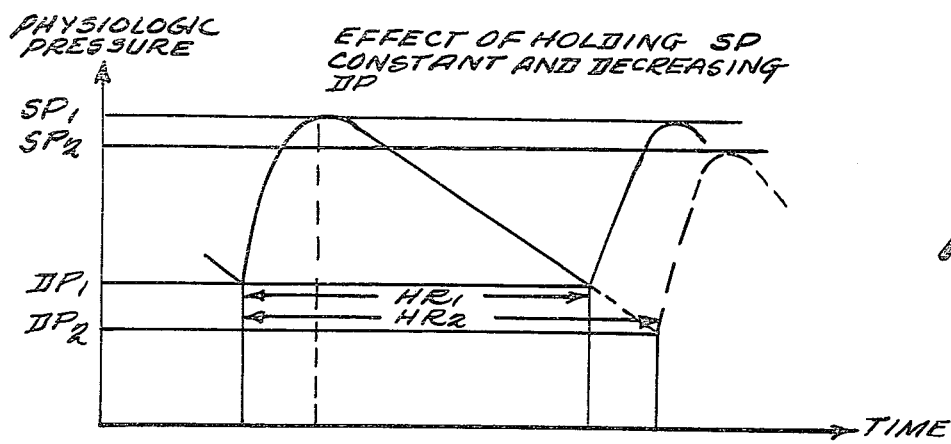

FIGS. 17 and 18 show the effect of holding SP constant and initiating the next cycle at a different DP. If the DP is increased, then the PCT would decrease (e.g., the PRR would increase) as seen in FIG. 17. The converse is shown in FIG. 18.

Figures 19, 20:
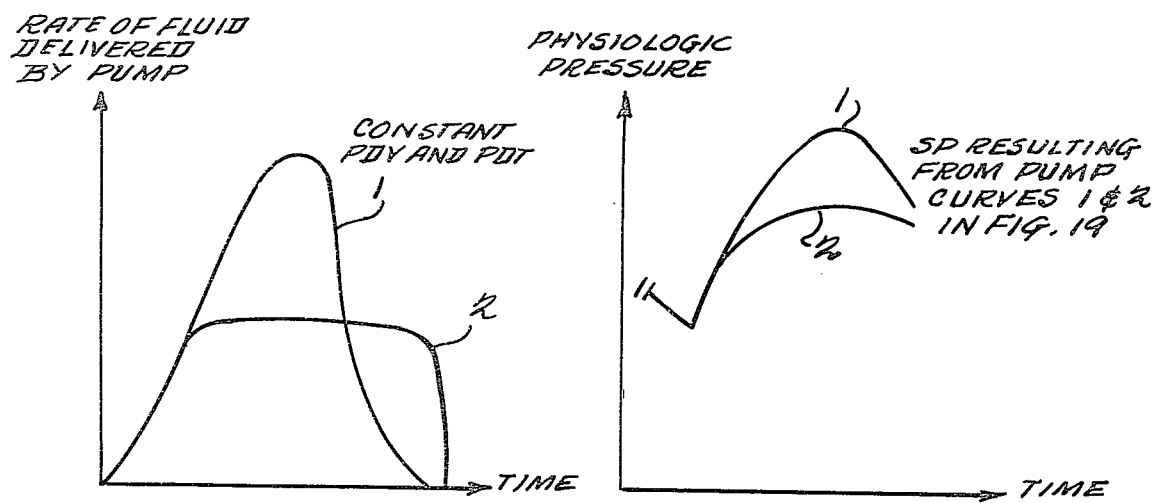

FIGS. 19 and 20 show the effect of changing the pump delivery speed curve while PDV and PDT are constant. In this case, SP will increase as the fluid is delivered in a shorter period of time. This effect should be taken into account to optimize a pulsatile pumping system.

Prior approaches to control of a pulsatile pump system have, in effect, used only a single variable change for control purposes. Typically, only a single pump parameter such as PRR (or at best, PRR tied to PDV) have been controlled. No known prior attempt has been made to change even these two variables independently. In order for a feedback system with multiple degrees of freedom to converge, there must be an ability to vary multiple inputs.

The present invention provides a closed loop feedback mechanism which mimics the heart and its controls. In the preferred embodiment, PDT and PDV are varied independently at a constant DP to obtain a desired preset SP and HR, as well as DP. But this is only a specific case of the more general principles disclosed.

There are a multiplicity of combinations of the aforementioned physiologic and pump parameters and others (some of which may be redundant), which could be used to regulate an automatic feedback controlled perfusion mechanism according to the sets of predetermined logic rules.

In the most general case, an adaptive learning machine would be given all the possible pump variables. It would be given the desired HR, SP, and DP and perhaps other physiologic parameters. The machine then, by trial and error, would attempt a solution. By measuring its own performance, the learning machine would construct its own set of logic rules for a given set of imposed conditions. But even this generalized type of solution would be a combination of the general logic rules used and described herein.

From the above explanation of FIGS. 3-20, it should now be appreciated that detected deviations in plural physiologic parameters can be simultaneously corrected by making appropriate changes in independent plural pump operating parameters. For example, if SP needs to increase and HP needs to decrease, the PDV can be increased while the PCT is decreased (e.g., by decreasing pump ejection time PET or PROT). Alternatively, in this instance, merely decreasing PET alone would tend to correctly change both SP and HP. Depending upon the choice of physiologic and pump parameters, literally endless combinations of logical rules can be formulated to correctly close the control loop and insure the simultaneous convergence of plural physiologic parameters to "goal" values. However, to handle plural physiologic parameters in all cases, there should be plural independently controlled pump parameters.

Using the preferred choice of SP, DP and HP (or HR) physiologic parameters and PDS, PDV and PCT pump parameters, the following tabulation summarizes one possible set of logical rules for controlling the pump so as to maintain the desired physiologic parameters (" ↑ " represents "increase", " ↓ " represents "decrease and "—" represents "no change", and "=" represents a constant fixed parameter):

| Detected deviation of SP, DP and/or HP from desired normal values | | | Possible controlled change in PDS, PDV and/or PCT to correct for detected physiological deviation | | |
|---|---|---|---|---|---|
| SP | DP | HR(1/HP) | PDS | PDV | PCT |
| ↑ | = | ↑ | ↓ | — | = |
| ↓ | = | ↓ | ↑ | — | = |
| ↑ | = | ↑ | — | ↓ | = |
| ↓ | = | ↓ | — | ↑ | = |
| ↑ | = | — | ↓ | ↓ | = |
| ↓ | = | — | ↑ | ↑ | = |
| — | = | ↑ | ↓ | ↑ | = |
| — | = | ↓ | ↑ | ↓ | = |
| ↑ | ↓ | = | ↓ | — | = |
| ↓ | ↑ | = | ↑ | — | = |
| ↑ | ↑ | = | — | ↓ | = |
| ↓ | ↓ | = | — | ↑ | = |
| ↑ | — | = | ↓ | ↓ | = |
| ↓ | — | = | ↑ | ↑ | = |
| — | ↓ | = | ↓ | ↑ | = |
| — | ↑ | = | ↑ | ↓ | = |

Referring to FIGS. 21 and 22, a heart pump system constructed according to the invention is shown. The system comprises a heart pump 10 (see FIGS. 1 and 2), which is physically coupled to a patient's circulatory system.

The meaning of some of the symbols on the block diagram are briefly given in the following table:
$Q_f$ = A signal indicating the "Fill" mode
$Q_s$ = A signal indicating the "start" mode
$Q_r$ = A signal indicating the "run" mode
$Q_p$ = A signal indicating either the "start" or "run" mode.

Typically, $Q_f$ is initially generated even prior to $Q_s$. After $Q_s$, $Q_r$ is generated. $Q_p$ is present when either $Q_s$ or $Q_r$ is present. The meaning of other symbols used in the diagrams will become apparent in the following discussion.

The control system includes circuitry for monitoring the patient's blood pressure comprising a conventional pressure transducer 102 which produces a voltage signal proportional to blood pressure, a lowdrift, high common mode rejection amplifier 104 for amplifying the output to transducer 102, and a 4-pole Butterworth low pass filter 106 for filtering the output of amplifier 104. Transducer 102 and amplifier 104 are of conventional design, such as, for example, a Statham Model No. P23DB and a Burr-Brown No. 3625B, respectively. Transducer 102 further includes any necessary power supplies which may be required for the particular transducer selected. The component values of filter 106 are selected such that the output of filter 106 is 3 dB down at 20 Hz.

A comparator 110 compares the output signal P of filter 106 with a voltage signal $DP_d$, produced by a diastolic dial 112. This manually preset input corresponds to the diastolic pressure DP desired for the patient. A comparator module 114, compares the output P with a voltage signal $SP_d$, produced by a systolic dial 116 corresponding to the systolic pressure SP desired for the patient.

Comparator 110 is biased such that an output signal $P_c$ is generated so long as the level of output P is greater than a predetermined value slightly higher than the level of signal $DP_d$. The biasing of comparator 110 is adjusted so that the piston of pump 10 will be coupled to its driving motor slightly before the desired pressure DP is reached and the piston will reach its bottom dead center position at the same time the desired pressure DP is reached, as will be described in more detail hereinbelow.

In a similar manner, comparator 114 produces two outputs, the first if signal P is greater than signal $SP_d$ by a predetermined amount, and the second if signal P is less than signal $SP_d$ by a predetermined amount. Thus, while signal P is within a preselected range interval above or below the level of signal $SP_d$, no output is produced by comparator module 114.

Dials 112 and 116 may be implemented as conventional manually adjustable voltage dividers, such as the "Digivider" manufactured by the Digitran Co. A conventional digital voltmeter (DVM) pressure display 108 displays the signal P as a pressure when gated by a timing pulse $T_{min}$, described hereinbelow. Since pulse $T_{min}$ occurs at the bottom of the stroke of pump 101, display 108 thus indicates the patient's actual diastolic pressure DP. A conventional peak detecting circuit 120 monitors peaks in signal P, representing the patient's pressure SP, and produces corresponding outputs which are displayed as pressures by a conventional DVM systolic pressure display 122.

Conventional systolic pressure latches 118 produce control signals $P_{HL}$ and $P_{LL}$. Module 118 comprises two conventional R-S flip-flops, gated by a mode control signal $Q_r$ and reset by timing pulse $T_{min}$. When reset, both R-S flip-flop outputs are low, regardless of the operating mode. When signal $Q_r$ is present, the outputs from comparator 114 are gated to the "set" inputs of the corresponding module 118 flip-flops. If comparator 114 produces the $P_H$ output, one flip-flop is set, and produces signal $P_{HL}$. If module 114 produces the output $P_L$, the other flip-flop is set and produces signal $P_{LL}$. If comparator 114 produces neither output $P_H$ or $P_L$, both flip-flops remain in their reset condition, producing no output. The signals $P_{HL}$ and $P_{LL}$ thus represent conditions wherein the patient's actual blood pressure is beyond a tolerable deviation from the desired pressure $SP_d$.

Clock modules 200 and 202 are conventional clock and divider circuits which provide synchronized 1 KHz, 100 Hz, 10 Hz, and 1 Hz clock signals for use by various components of the control system. Depending on whether operation is, respectively, in the automatic (AUTO) or manual (MAN) mode of operation (to be described), a conventional cycle timer gating module 204 selects between the 1 KHz and 10 Hz clock signals for input to a cycle time counter 206 comprising conventional counters and latches.

In the AUTO mode, gating module 204 is controlled by a mode indicating signal $A_{ct}$ which gates the 1 KHz clock signal into counter 206 continuously, and which also directs the counters in module 206 to count "up". In the MAN mode, two manually controlled signals, +HR and −HR, control module 204, such that the 10Hz clock signal is gated into counter 206 only when signal +HR or −HR is activated. In addition, signals +HR and −HR control the direction of count by counter 206.

Counter 206 is also controlled by three signals $Q_m$, $T_{max}$, and $T_{reset}$, generated by other modules to be described. When in the AUTO mode, pulse $T_{max}$ gates the module 206 latches on momentarily, thus setting the output latches with the count then existing in the counters, which count represents the period of the previous cycle of operation. Pulse $T_{reset}$, occurring shortly after pulse $T_{max}$ causes the counters in module 206 to be reset in readiness for the next cycle. When in the MAN mode, mode control signal $Q_m$ gates the output latches continuously so that the output of module 206 follows the instantaneous count in the counters.

The digital count output of the module 206 latches is converted by a conventional digital-to-analog converter module 208 to a voltage signal $V_{ct}$ representing the patient's heart rate HR. $V_{ct}$ from module 208 is displayed by a conventional DVM heart rate display 212 to produce an indication of HR and forms an input to a conventional comparator module 216. Comparator module 216 compares heart rate signal $V_{ct}$ with a signal $HR_d$, representing the desired heart rate, produced by a heart rate dial 214 similar to dials 112 and 116 described above. Comparator module 216 produces an output $R_h$ if amplified signal $V_{ct}$ is greater than signal $HR_d$ by a predetermined amount, and an output $R_L$ if amplified signal $V_{ct}$ is less than signal $HR_d$ by a predetermined amount.

A start/mode control module 300 comprises conventional R-S flip-flops. Module 300 produces five mode control gating signals, $Q_f$, $Q_m$, $Q_p$, and $Q_s$ (and their inversions $\bar{Q_f}, \bar{Q_m}, \bar{Q_p}, \bar{Q_r}$, and $\bar{Q_s}$) in response to three manually controlled inputs FILL, START, and AUTO/MANUAL as well as signal $P_c$ from comparator 110. A signal TDR initializes control module 300 when the system is first energized.

A clutch control module 302 comprises conventional gating circuitry which produces an output R in response to a timing pulse $T_o$ (from pulse generator 502) and gating signals $Q_f$, $Q_p$, and $Q_r$ from mode control module 300. Module 302 also produces output R in response to manually-controlled input MANUAL START. A motor 358 drives the piston of pump 10 when mechanically coupled thereto by a conventional clutch-brake assembly 304. Output R from module 302 controls engagement of clutch-brake 304 and when operating in the FILL-AUTO or START-AUTO modes it is produced continuously to engage the clutch-brake 304 continuously.

When operating in the RUN-AUTO or MAN modes, output R is produced in the form of a pulse in response to pulse $T_o$, which causes clutch-brake 304 to be engaged for only a predetermined duration, and then disengaged automatically until the next recurrence of output R. The predetermined duration of clutch-brake engagement is such that pump 10 is disengaged from motor 358 at, or shortly after, the piston 36 passes its top dead center position, and such that piston 36 does not pass its bottom dead center position before stopping even when being driven at maximum speed by motor 358. The automatic disengagement of clutch-brake 304 at particular phases of pump operation may be effected in any known manner, such as, for example by cam-actuated switches.

The stroke length of the piston 36 may be varied in order to vary the PDV. The linkage which changes the stroke length is driven by a conventional volume change motor 310. A volume change logic module 306 comprises conventional gating circuits and a monostable (one-shot) multivibrator. It produces volume change control signals $+V_d$ and $-V_d$ to control the drive circuit 308 for motor 310 in accordance with the various indicated control signal inputs.

When operating in the FILL-AUTO mode, the gating signal $Q_f$ causes the signal $-V_d$ to be generated continuously, which in turn causes motor 310 to reduce the PDV continuously until minimum PDV is attained. When operating in the START-AUTO or RUN-AUTO modes, either signal $+V_d$ or $-V_d$ is produced when gated by a timing signal $T_{max}^+$ for a duration determined by the time constant of the module 306 one-shot, and also depending on whether control signal $+\Delta V$ or $-\Delta V$, respectively (produced by logic box 510) is present. When operating in the MAN mode, gating signal $Q_m$ enables the manually controlled inputs $+V$ and $-V$, which cause signals $+V_d$ and $-V_d$ to be generated, respectively, for a duration corresponding to that of signals $+V$ and $-V$. The 1 KHz clock signal is provided for the module 306 one-shot.

A speed control logic module 350, in conjunction with a conventional speed control counter module 352, digital-to-analog (D/A) converter module 354, and silicon-controlled rectifier (SCR) motor control 356, controls the speed of motor 358, and thus the PDS. Speed control module 350 comprises conventional gating circuitry controlled by timing pulse $T_{max}^+$ and mode control signals $Q_m$ and $Q_p$ produced by module 300. When signal $Q_m$ is absent, pulse $T_{max}^+$ causes the control signal, if any, which is then being produced by logic box 510 to increment (signal $-\Delta N$) or decrement signal $+\Delta N$) the module 352 counters by one count, and thus decrease or increase respectively, the speed of motor 358. When signal $Q_m$ is present, manually controlled signals $+N$ and $-N$ are enabled and pulse $T_{max}{}^+$ causes whichever of the signals $+N$ or $-N$ is then being activated to decrement or increment counters 352 and thus control the speed of motor 358. Signal $Q_p$ enables module 350; its absence blocks any of the control signals $+\Delta N$, $-\Delta N$, $+N$, and $-N$, from influencing counter module 352.

D/A converter module 354 comprises a conventional D/A converter and diode shaping network which convert the count in the module 352 counters to an analog signal which is used by the conventional SCR motor control 356 to control the speed of motor 358.

The piston 36 is mechanically connected via a conventional mechanical linkage 360 to the wiper of a sliding potentiometer (pot) 400, which, by means of conventional voltage divider circuitry, produces a voltage output corresponding to the position of the piston. The output of pot 400 is processed by a conventional peak-to-peak detector 402, which produces a voltage corresponding to the length of the stroke of the piston, and thus directly proportional to the PDV. The output of detector 402 is displayed on a conventional DVM 404, which is gated by timing signal $T_{max}$.

A conventional optical position detector 520 comprising a rotating light chopper coupled to the piston shaft and a photocell detects the top dead center (TDC) and bottom dead center (BDC) positions of the pump piston during its stroke. Conventional pulse circuits 522 produce the two timing pulses, $T_{max}$, corresponding to the TDC position of the pump piston and $T_{min}$, corresponding to the BDC position thereof. Signal $T_{max}$ is further processed by a conventional pulse generator 524, which produces sequentially two further timing pulses, $T_{reset}$ and $T_{max}{}^+$ delayed in time from $T_{max}$.

$T_{reset}$ and $T_{max}{}^+$ are thus generated in this mode during the run-off time (PROT) portion of each pump cycle. The functions of the various timing pulses are described in more detail in connection with the description of the system components controlled thereby.

A pulse generator module 502 produces timing pulse $T_o$, used by the remainder of the system to initiate each pump cycle during the RUN-AUTO mode, and a signal $A_{ct}$, which is an internal control signal indicating the AUTO mode of operation. When operating in the AUTO mode, generator 502 produces signal $T_o$ when the output $P_c$ from comparator 110 switches "low," or automatically, should diastolic pressure DP fail to reach, within a predetermined time limit, the predetermined level slightly higher than the desired value $DP_d$ at which the comparator 110 output switches. When operating in the MAN mode, a signal $T_{om}$ produced by a voltage controlled oscillator (VCO) module 500 constitutes signal $T_o$. VCO module 500 has a voltage control input to which is applied the output $V_{ct}$ from digital-to-analog converter module 208, which controls the frequency at which $T_{om}$ is generated. When switched from the AUTO mode to the MAN mode, $T_{om}$ is generated at the same frequency at which $T_o$ was being generated before shifting to the manual mode, until manually incremented or decremented, as described hereinbelow. In the AUTO mode, control signal $A_{ct}$ inhibits oscillation of VCO module 500. Referring to FIG. 23, the relationship between maximum and minimum pump strokes, timing signals $T_{max}$, $T_{min}$, and $T_o$ are shown.

Logic box 510, comprising combinational logic circuitry is the heart of pump control system, generating PDV control signals $+\Delta V$ and $-\Delta V$, and PET control signals $+\Delta N$ and $-\Delta N$ in response to input signals $P_{HL}$, $P_{LL}$, $R_H$, and $R_L$ and in accordance with the logical decision table:

Table 1

|  | $P_{LL}$ | SP equal to preset value | $P_{HL}$ |
|---|---|---|---|
| $R_L$ | $+\Delta N$ | $+\Delta N$ $-\Delta V$ | $-\Delta V$ |
| HR equal to preset value | $+\Delta N$ $+\Delta V$ | Nothing $-\Delta N$ | $-\Delta N$ $-\Delta V$ |
| $R_H$ | $+\Delta V$ | $+\Delta V$ | $-\Delta N$ | and in accordance with the corresponding Boolean equations:

$+\Delta N = P_{LL}R_H + R_L P_{HL}$ $-\Delta N = P_{LL}R_H + P_{HL}R_L$ $+\Delta V = R_H P_{HL} + P_{LL}R_L$ $-\Delta V = P_{HL}R_H + R_L P_{LL}$ (Equation 1)

The following Table 2 shows the necessary actions to be taken by the system depending on whether input $R_H$ or $R_L$ is present, or both inputs $R_H$ and $R_L$ are absent representing, respectively, a high, low or satisfactory heart rate HR, or on whether input $P_{HL}$ or $P_{LL}$ is present, or both inputs $P_{HL}$ and $P_{LL}$ are absent representing, respectively, high, low or satisfactory systolic pressure SP. DP is assumed to be maintained at a constant value:

Table 2

|  | SP ↑ | SP satisfactory | SP ↓ |
|---|---|---|---|
| HR ↑ | PDT ↓ | PDT ↓ PDV ↓ | PDV ↓ |
| HR satisfactory | PDT ↓ PDV ↑ | no change | PDT ↑ PDV ↓ |
| HR ↓ | PDV ↑ | PDT ↑ PDV ↑ | PDT ↑ |

Note:
↑ = "increased" and ↓ = "decreased"

It should be noted that N represents the speed of systolic ejection (or pump delivery speed PDS) and not the time of duration of systolic ejection, and it is therefore the reciprocal of PDT discussed hereinabove. Logic box 510 produces a further output signal OK when systolic pressure SP and heart rate HR are both satisfactory. Gating signals $Q_s$ and $Q_m$ either block input signals to, or inhibit output signals from, logic box 510 when the system is being operated in its various modes.

A conventional ejection time counter module 526, gated off and on respectively by signals $T_{max}$ and $T_{min}$, and driven by the 100 Hz clock signal produced by divider 202, produces a digital output representative of the PDT of the pump (corresponding to the systolic ejection time of the physiologic blood pressure wave) which is displayed on a conventional DVM display 528.

Three alarm circuits 600, 602, and 604, comprising conventional gates, counters, and flip-flops, monitor the various operations of the control system, and produce audible and visual alarms, X, Y, and Z, respectively, either when predetermined selected conditions are not reached by the pump system or when the system departed from a desired operating mode for a period longer than a predetermined time.

The interrelationship of the various elements of the system just described are more clearly related by the following discussion of system operation.

It should be noted that while the functional blocks of FIGS. 21 and 22 have been described in terms of conventional digital and analog circuitry, a firmware programmed microcomputer could be substituted for most of the digital and timing functions performed. Of course a software programmed general purpose computer could also be employed if desired.

Having described each of the components of the pump system, its operation will now be described.

The pump system may be operated in any one of three automatic (AUTO) modes, or in a manual (MAN) mode. The three AUTO modes will be referred to as the FILL, START, and RUN modes, respectively.

When the pump system is first energized by means of power switch 342, which connects the system to power source 344, a time delay relay 340 produces a signal TDR, which initializes the various counters 206, 352, and 526, and sets the latches in mode control module 300 to the FILL state, wherein all mode control gating signals $Q_f$, $Q_p$, $Q_r$, $Q_s$, and $Q_m$ are preset. Dials 112, 116, and 214 are set by the operator with the predetermined desired values of diastolic pressure $DP_d$, systolic pressure $SP_d$, and heart rate $HR_d$, respectively. With the pump system in the initialized state just described, activation of the FILL input causes the generation of mode control signal $Q_f$, which results in the following:

1. Clutch control module 302 is caused to generate output R continuously. As a consequence, clutch-brake 304 is engaged continuously.
2. Since logic box 510 output signals $+\Delta N$ and $-\Delta N$ are blocked from influencing speed control counter module 352 during the FILL stage by the absence of signal $Q_p$, and since the speed control counters 352 are in an initialized state, pump motor 358 runs at a constant minimum speed.
3. Volume change motor 310 is caused to decrease the PDV until a minimum value is reached, at which time the FILL input can be deactivated.

As a consequence of the FILL mode of operation, pump 10 is primed. If the pump control system is in an AUTO mode, i.e., the AUTO/MAN input has not been actvated, then the START input can be enabled. Activation of the START input causes the generation of mode control signal $Q_s$, which results in the following:

1. Control signal $Q_p$, which is an internal control signal indicating the START of RUN modes, is "high." With signal $Q_p$ high, the FILL input is disabled, thus preventing accidental activation thereof and the consequent disruption of the operation of control system during the START or RUN states.
2. Signals $R_H$ and $R_L$ from comparator module 216 are blocked as inputs to logic box 510. Since the patient's systolic pressure SP is low during this stage, pressure latches 118 generate the signal $P_{LL}$. Logic box 510 accordingly generates both output signals $+\Delta V$ and $+\Delta N$ (refer to Table 1 and the condition $P_{LL}$ and HR equal to preset value. Speed control logic module 350 is gated on, and signal $+\Delta N$ is allowed to influence counter module 352, when gated by timing pulses $T_{max}^+$. Volume change logic module 306 produces $+V_d$ signals when triggered by timing pulses $T_{max}^+$.
3. Clutch control module 302 generates output R continuously, and clutch-brake 304 is therefore engaged continuously.
4. Under the direction of the output signals $+\Delta V$ and $+\Delta N$ from logic box 510, pump control logic 350 causes the speed of pump motor 358 to increase, which decreases the PET, and causes volume change motor 310 to increase the stroke of piston 736, which increases the PEV. With clutch-brake 304 constantly engaged, pump 10 runs continuously without waiting for diastolic pressure $DP_d$ to be reached in the patient's circulatory system.

When the patient's diastolic pressure DP becomes greater than the predetermined desired valve $DP_d$, indicated by signal $P_c$ going "low," the pump system automatically switches to the RUN stage.

It is to be noted that in order for the START switch to be operative, the PEV must be at a minimum and the FILL and AUTO/MANUAL inputs must not be activated.

When pump system switches to the RUN stage, control signal $Q_r$ is generated, which results in the following:

1. None of the logic box 510 input or output signals is blocked. Logic box 510 thus generates output signals to control pump 10 on the basis of which of the signals $P_{LL}$, $P_{HL}$, $R_L$, and $R_H$, are actually present as inputs and in accordance with the decision Table 1.
2. Timing pulse $T_o$ is not blocked from controlling clutch control module 302. As depicted hereinabove, output R is generated in the form of a pulse, which results in the engagement of the clutch-brake 304 for a predetermined time interval. During the interval clutch-brake 304 is engaged, pump 101 ejects a volume of blood in a time determined by the logic box 510 control signals generated during the previous cycle. During the interval clutch-brake 304 is disengaged before the occurrence of the next timing pulse $T_o$, signal $T_{max}^+$ triggers the changes, if any, to be made in the pump SET and SEV for the next pumping cycle, in accordance with signals generated by logic box 510.

Since, as was noted hereinabove, comparator 110 is biased such that output $P_c$ switches low slightly before the desired diastolic pressure $DP_d$ is actually reached, pulse $T_o$ is also generated slightly before pressure $DP_d$ is attained. This enables the piston 36 to be driven from the rest position attained following disengagment of clutch-brake 304 during the previous cycle to the BDC position, such that the piston is in its BDC position when the desired diastolic pressure $DP_d$ is attained.

In either the START or RUN stages of the AUTO mode, the operator may switch pump system to the MAN mode by activating the AUTO/MAN input.

Activating the AUTO/MAN input causes the generation of mode control signal $Q_m$, which causes the following:

1. Signal $A_{ct}$ is blocked from influencing the operation of the system.
2. All of the logic box 510 output signals are low. As a consequence, pump 10 operates at the same ejection speed and volume which the pump system had attained in the AUTO mode immediately prior to the activation of the AUTO/MAN input, unless manually changed.
3. Manually controlled signals $+V$, $-V$, $+N$, $-N$, $+HR$, and $-HR$ are enabled, allowing the operator to manually increment or decrement, by a predetermined amount, the ejection volume (PEV) and speed (PDS) of pump 10, and the interval between timing pulses $T_o$, as discussed hereinabove.

The values of dials 116, 112, and 214, representing the desired systolic pressure $SP_d$, diastolic pressure $DP_d$, and the heart rate $HR_d$ may be changed at any time by the operator during the operation of pump system in the AUTO mode by adjusting the appropriate dial. Should the value for $DP_d$ be changed such that timing pulse $T_o$ is not generated normally, it is generated automatically, as described hereinabove. In addition, clutch-brake 304 may be engaged manually in an emergency by actuating the MAN START input to clutch control module 304.

During operation, alarm signal Y is generated by module 602 if the time required to reach the RUN stage of operation, once the START stage has been initiated, exceeds a predetermined interval. Similarly, alarm signal Z is generated by module 604 if the time required to achieve the predetermined operating parameters exceeds a predetermined amount. Finally, signal X is generated by module 600 if, once having achieved the predetermined operating parameters, the system departs therefrom for more than a predetermined time period.

Figure 24:
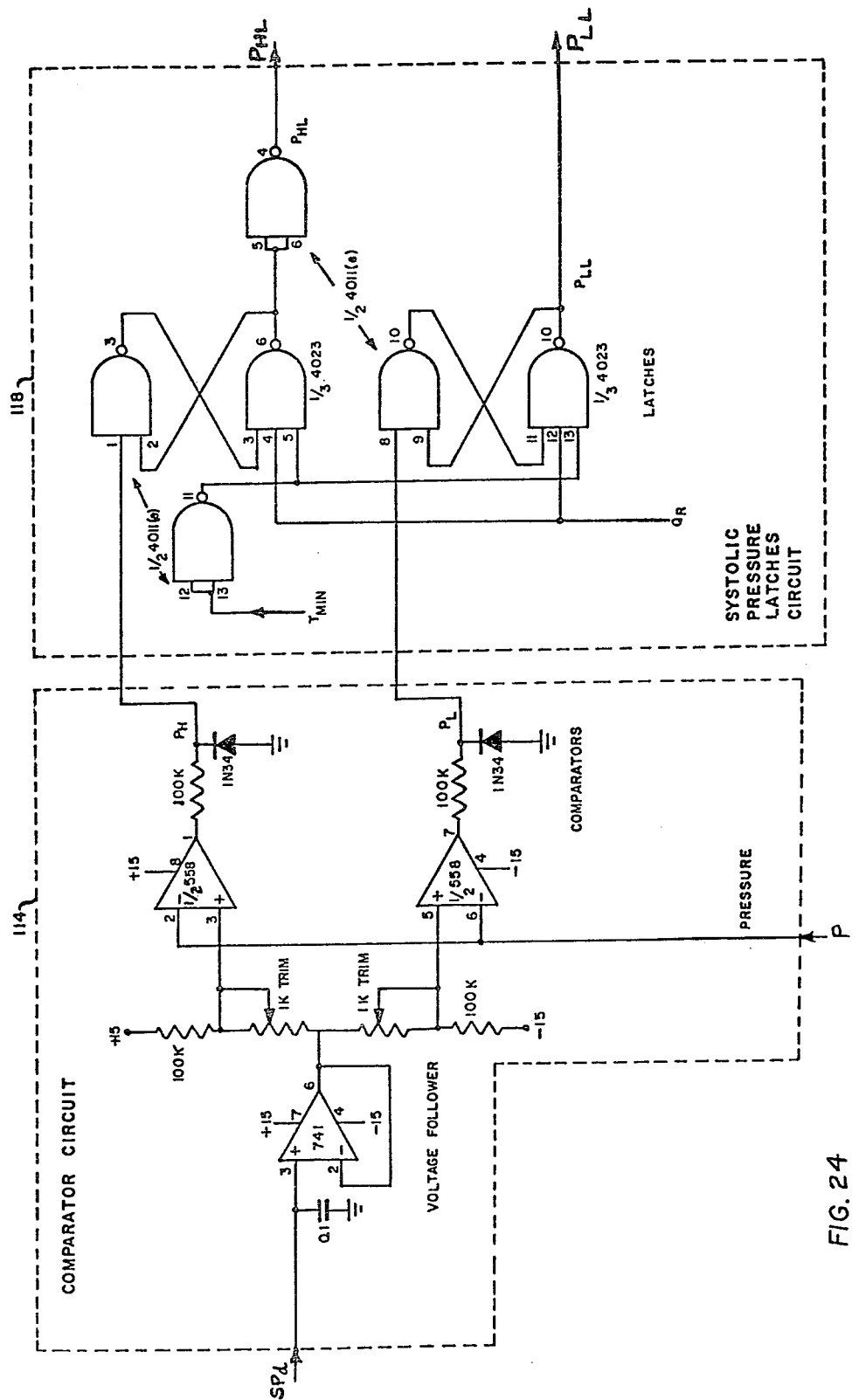
Figure 25:
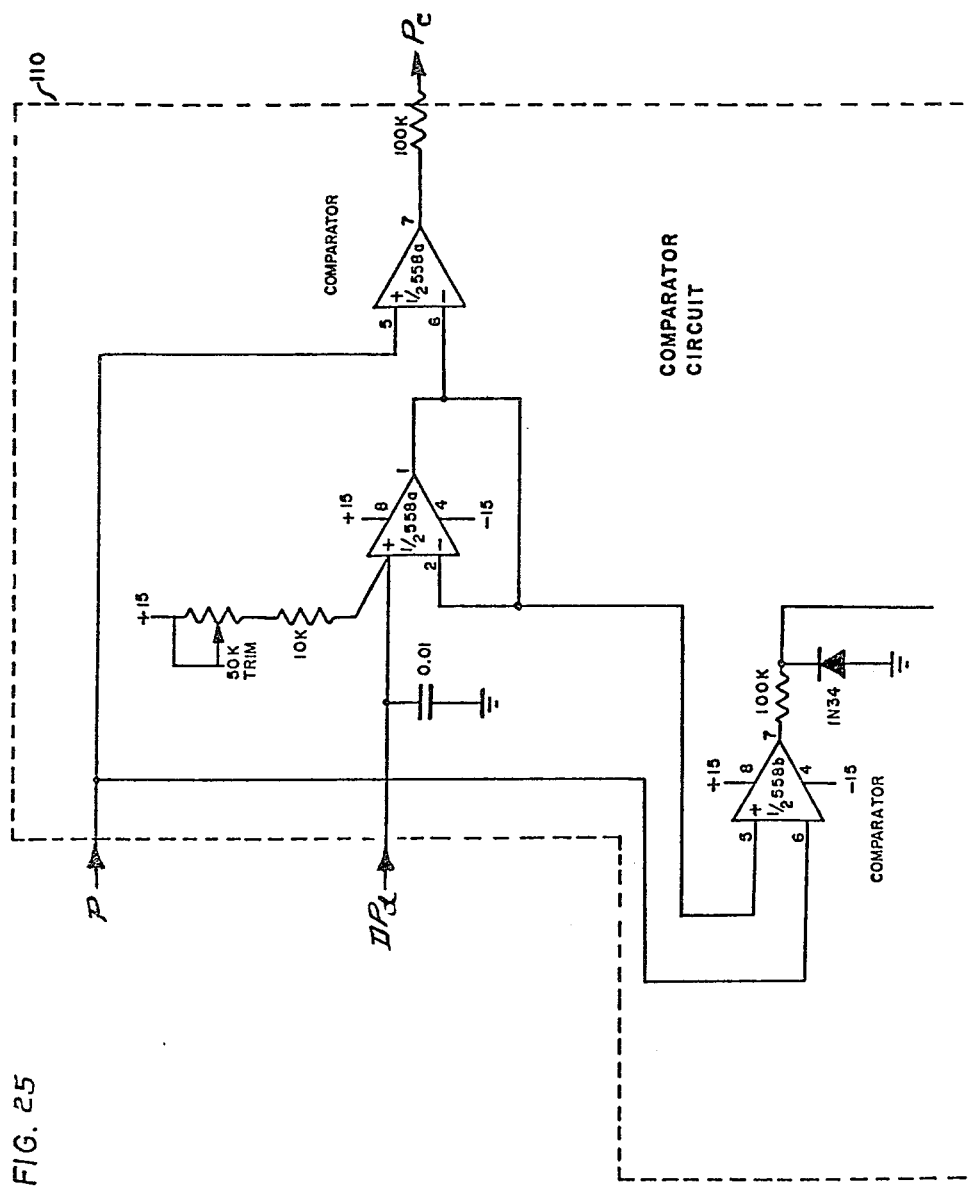
Figure 26:
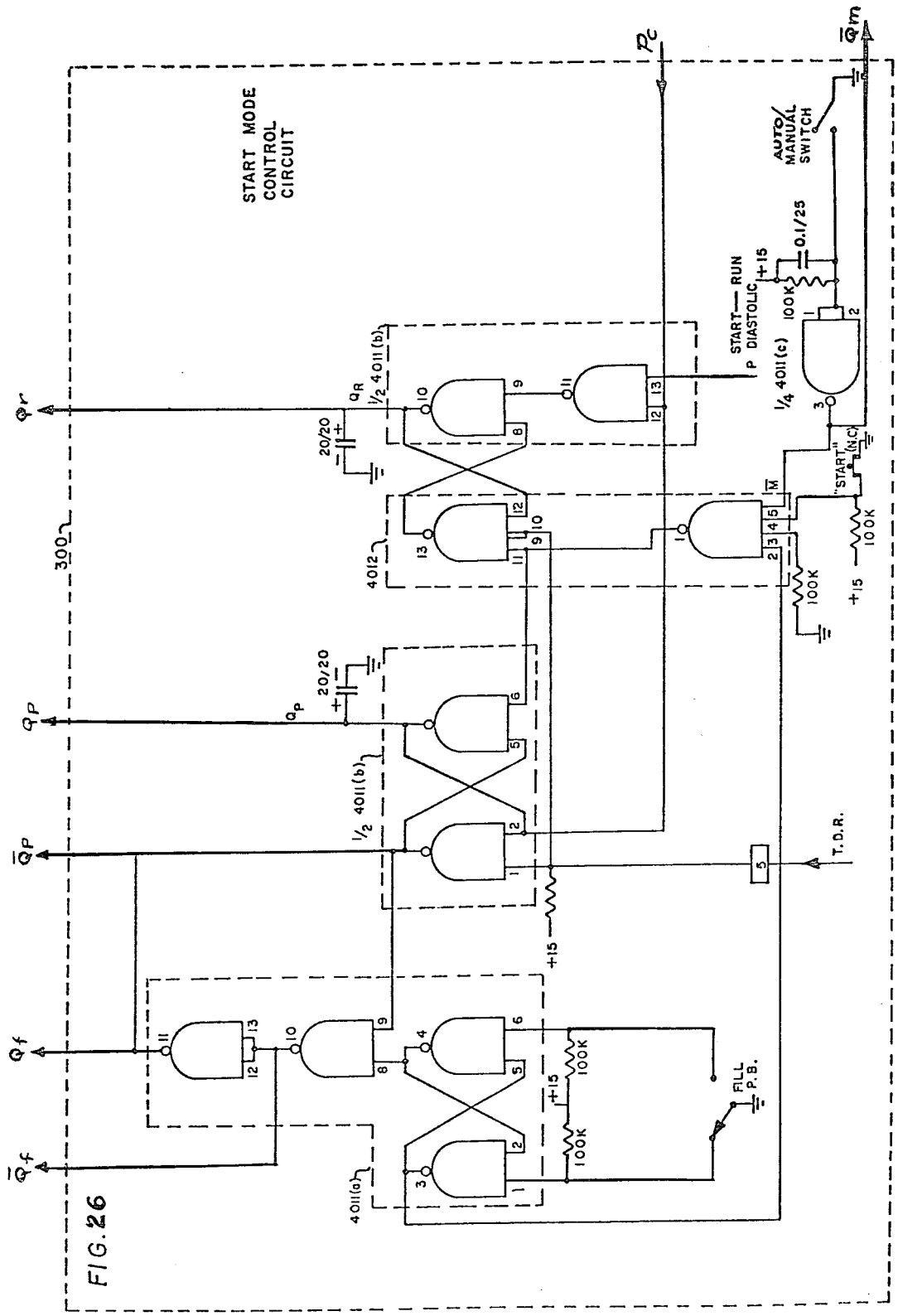
Figure 27:
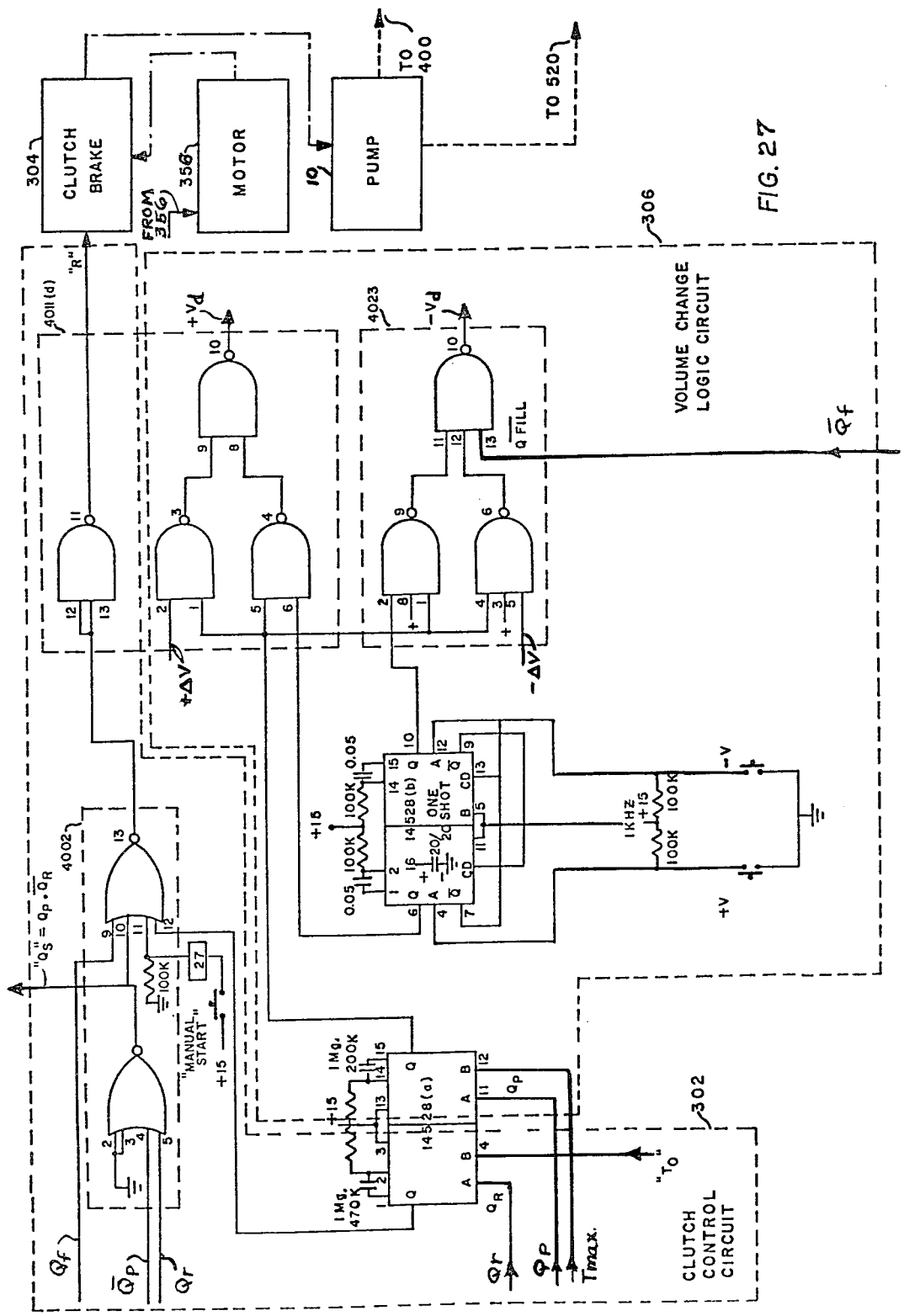
Figure 28:
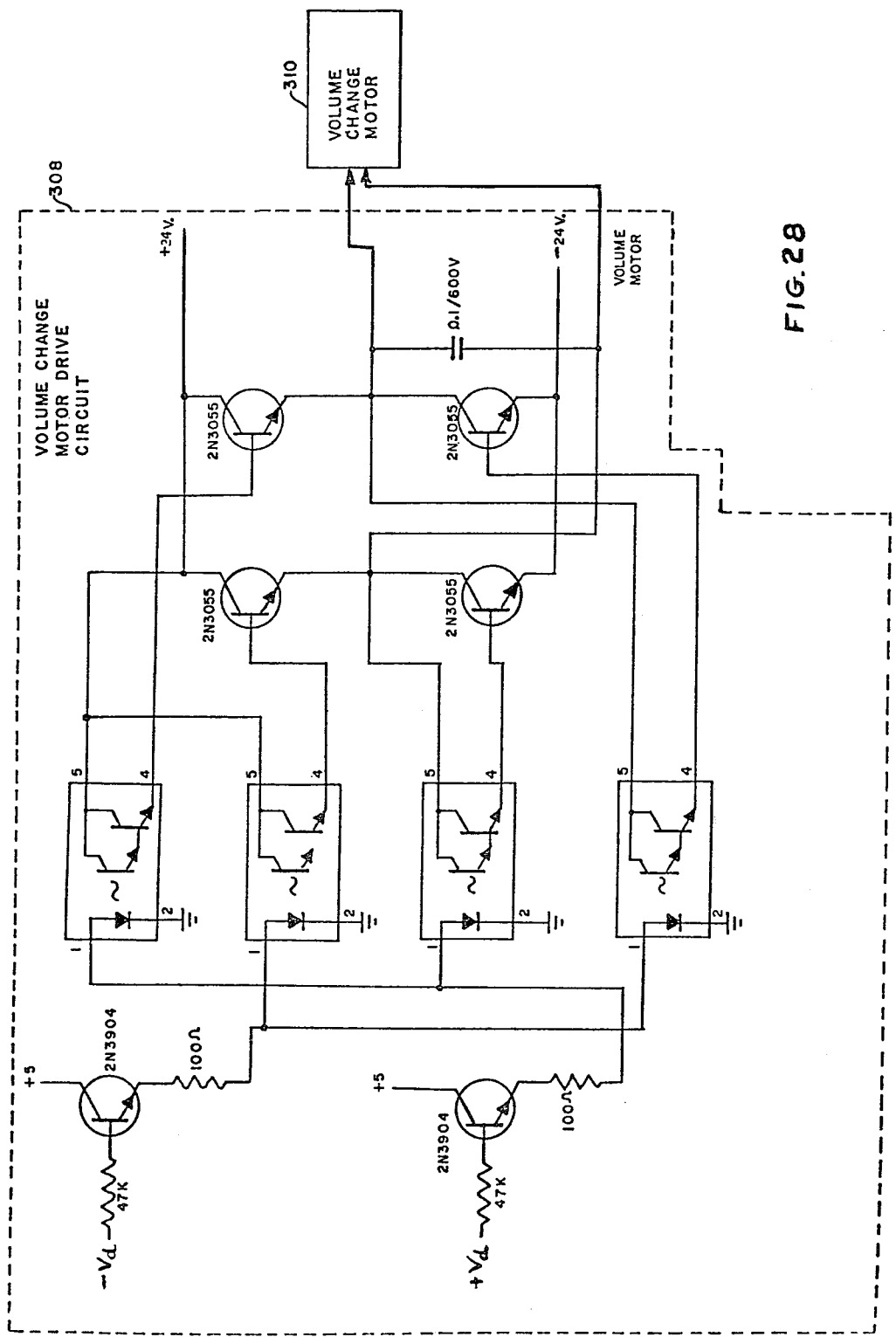
Figure 29:
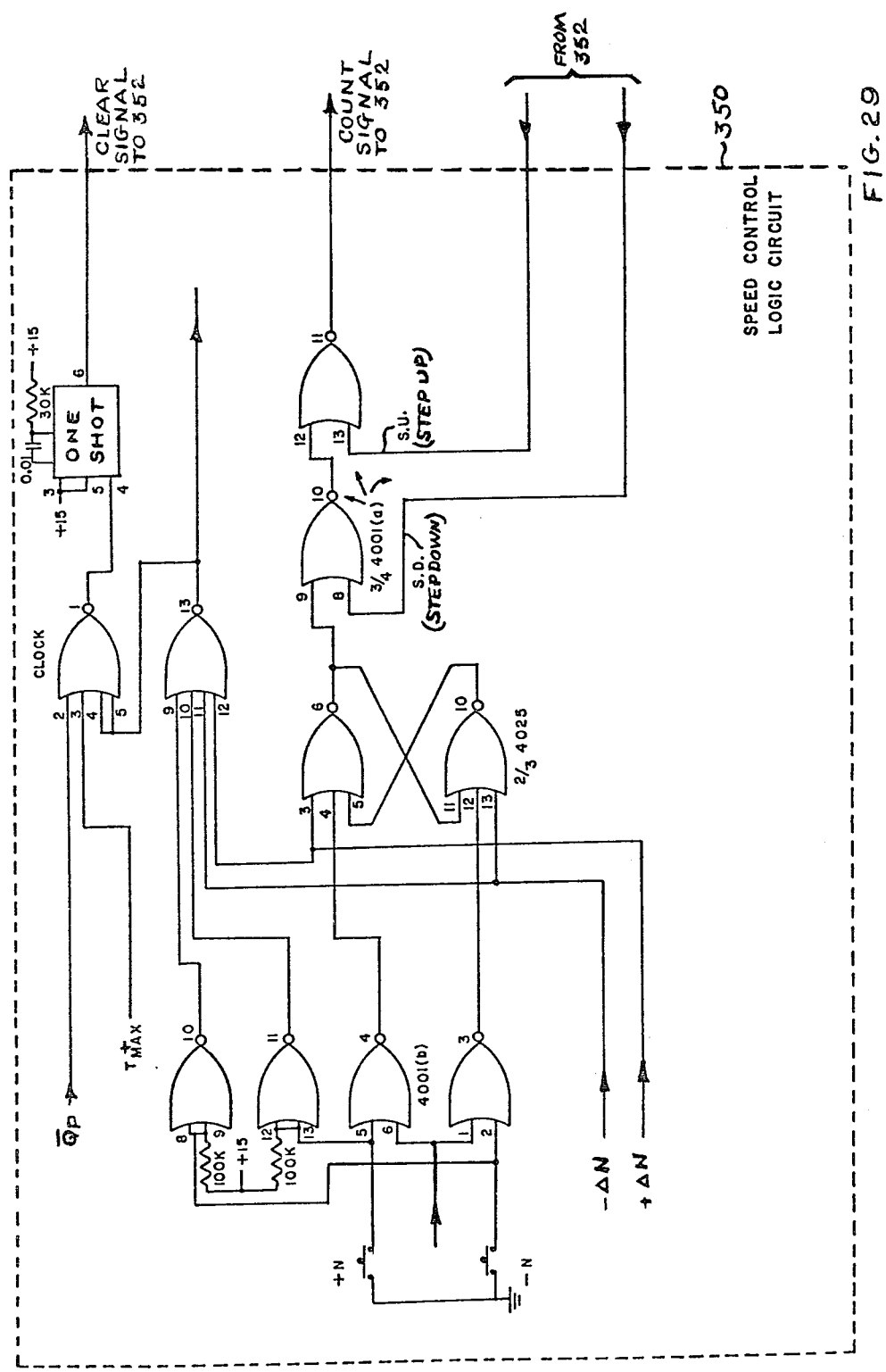
Figure 30:
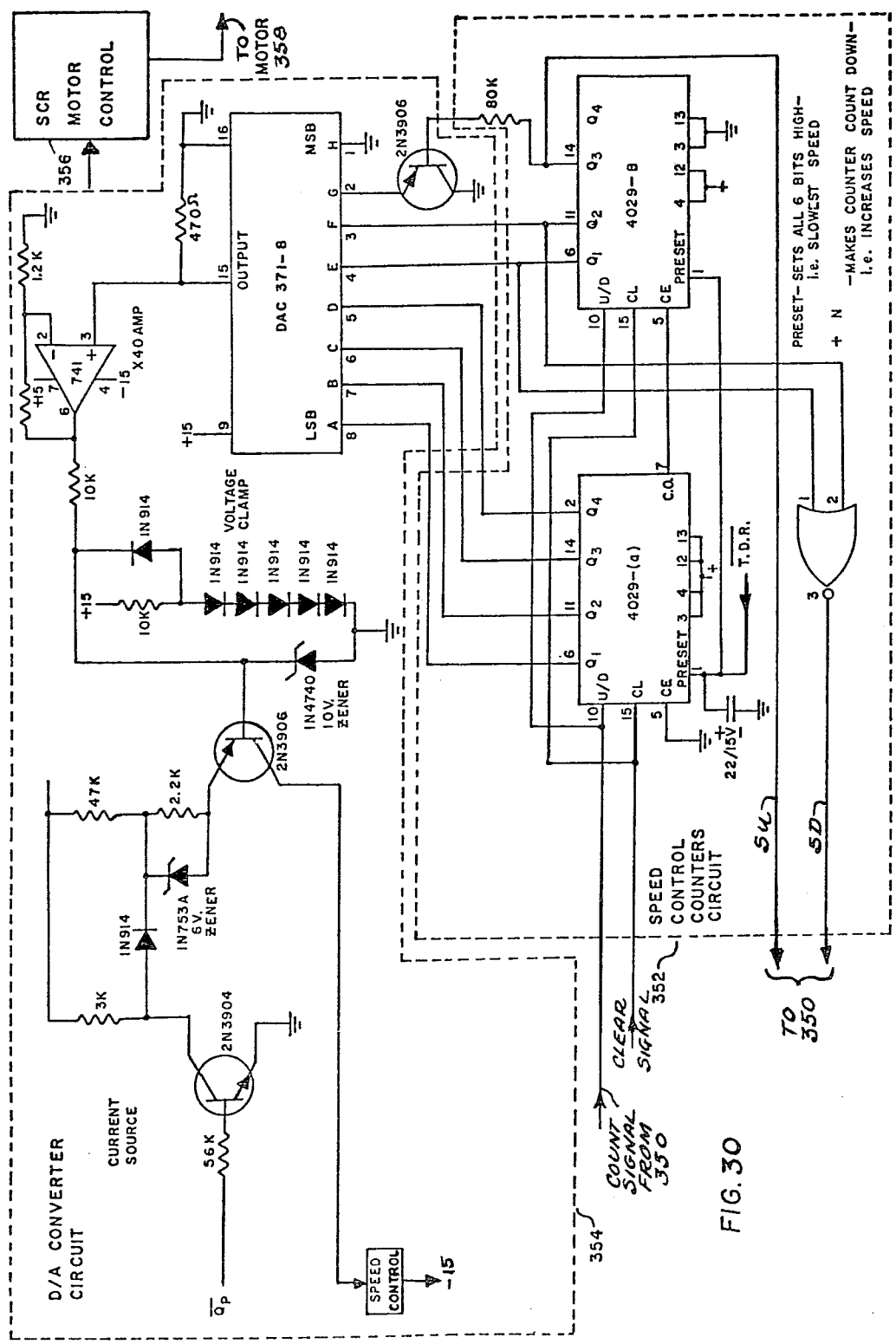
Figure 31:
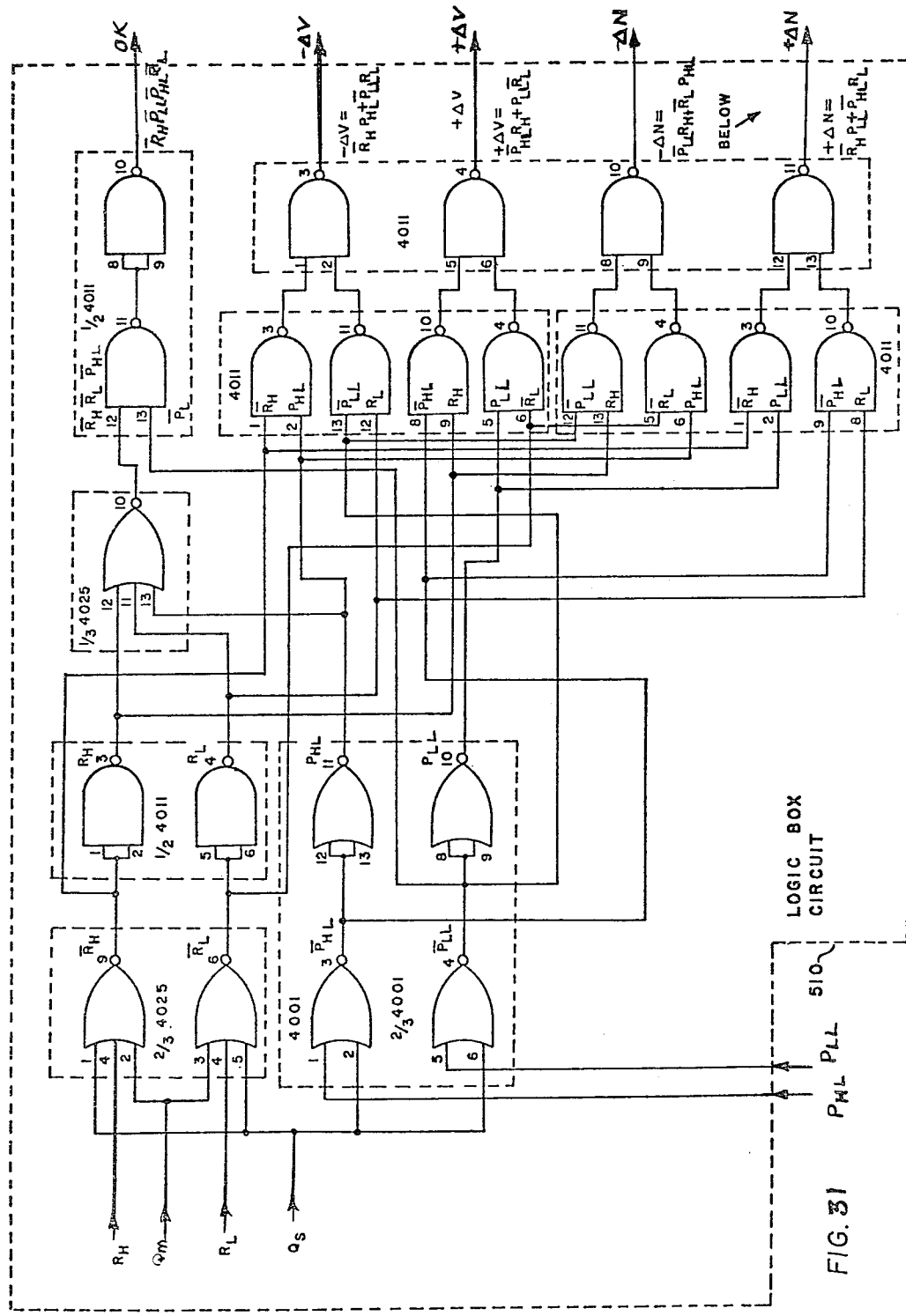
Figure 32:
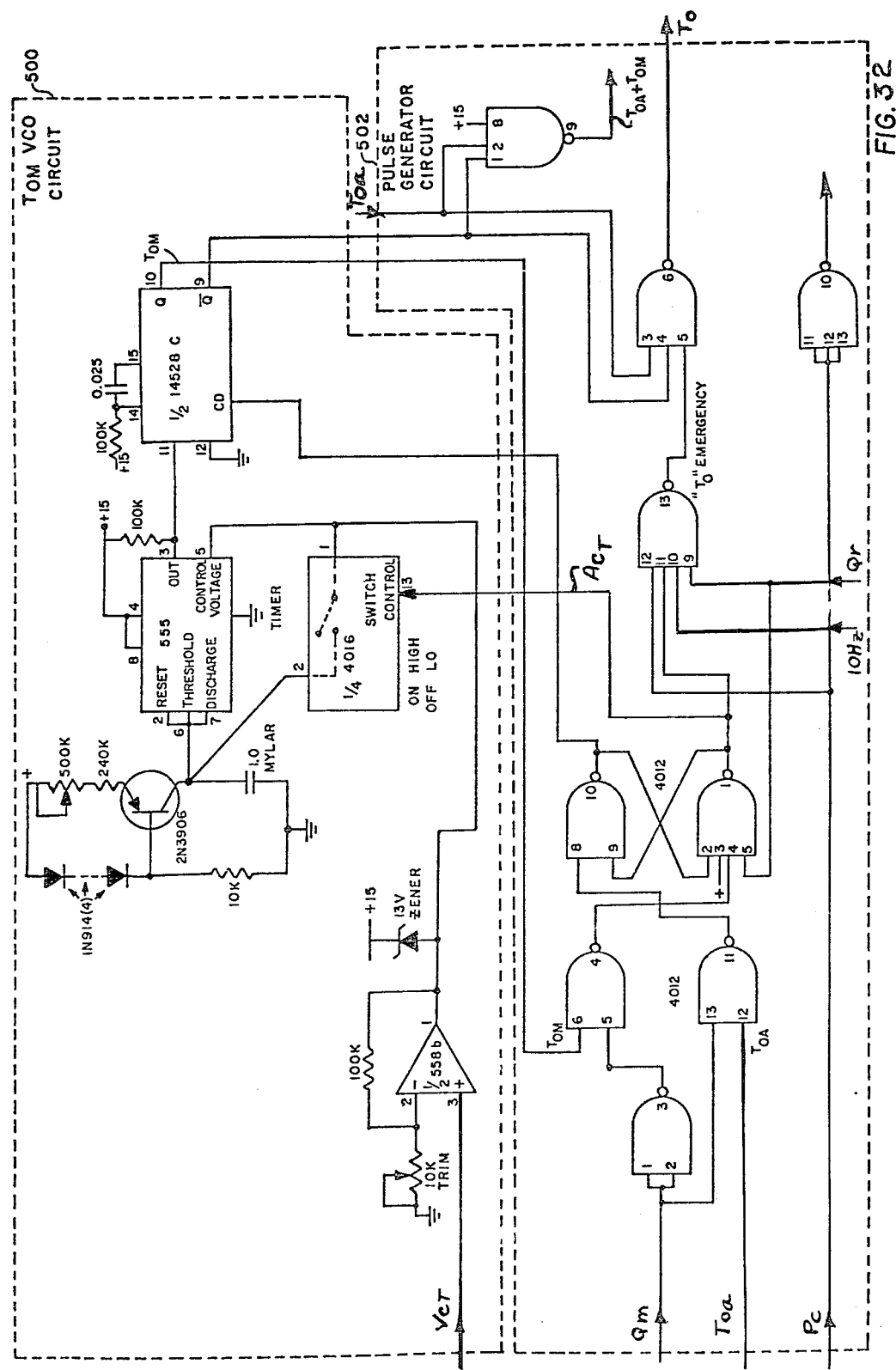
Figure 33:
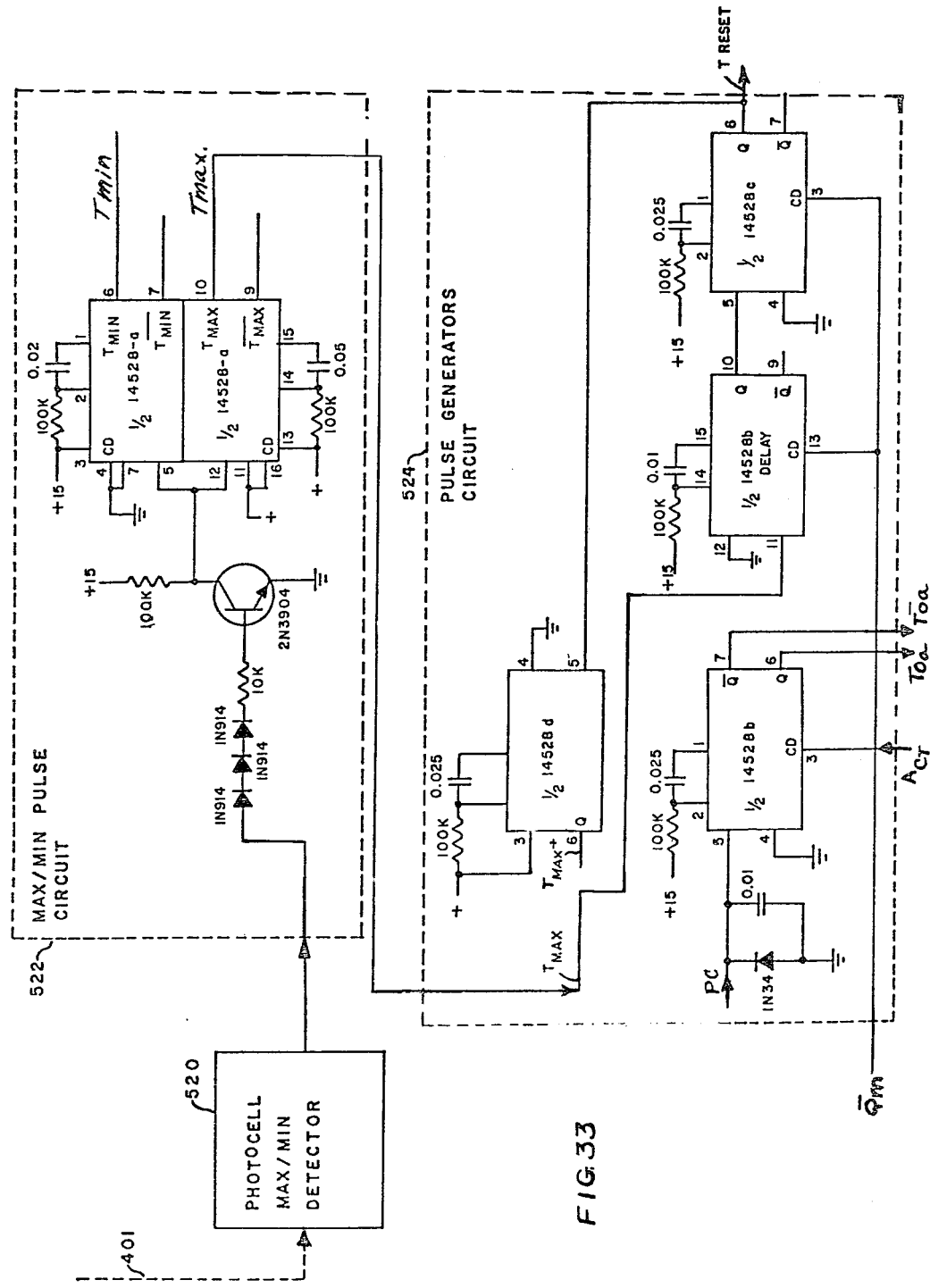
Figure 34:
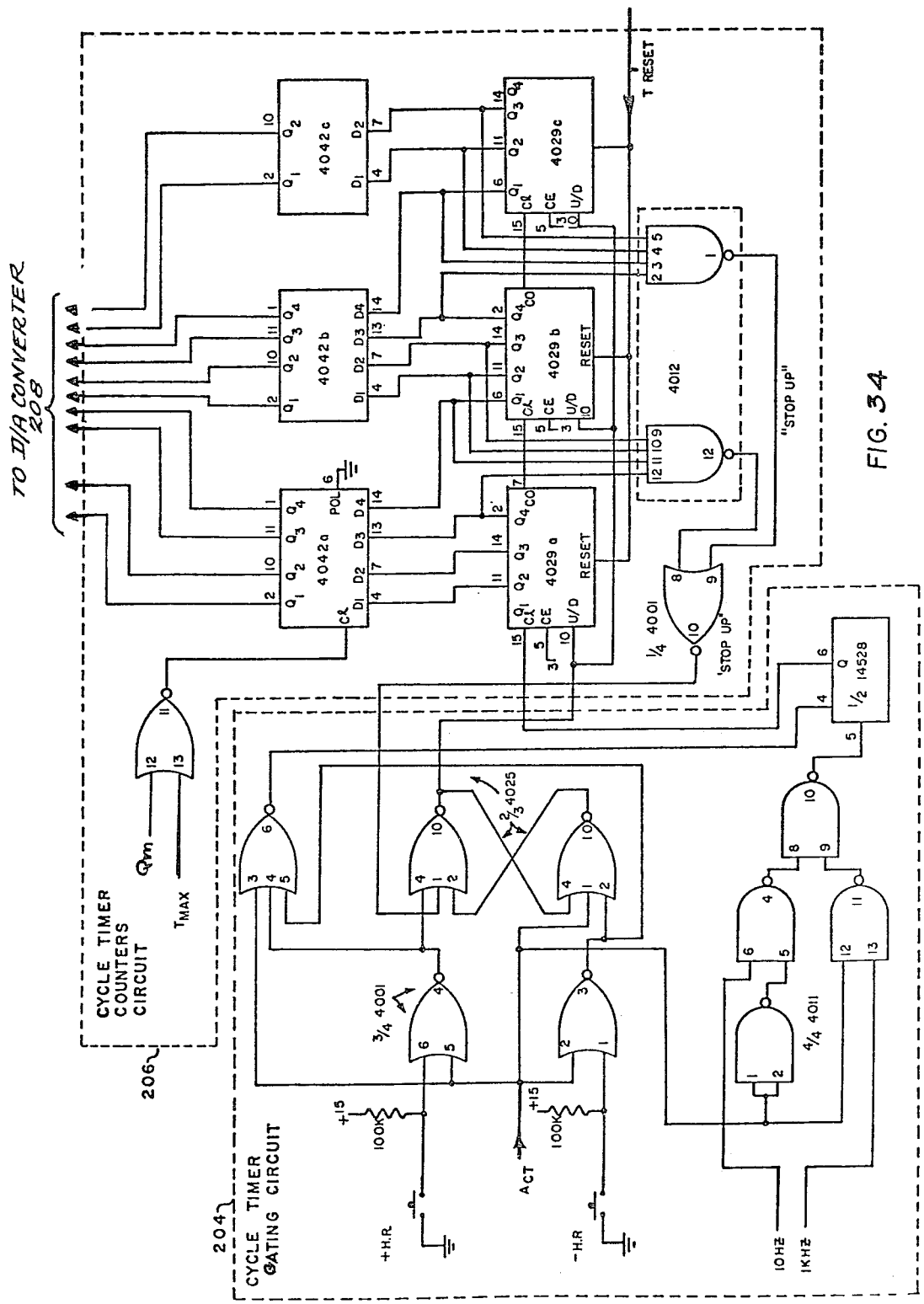
Figure 35:
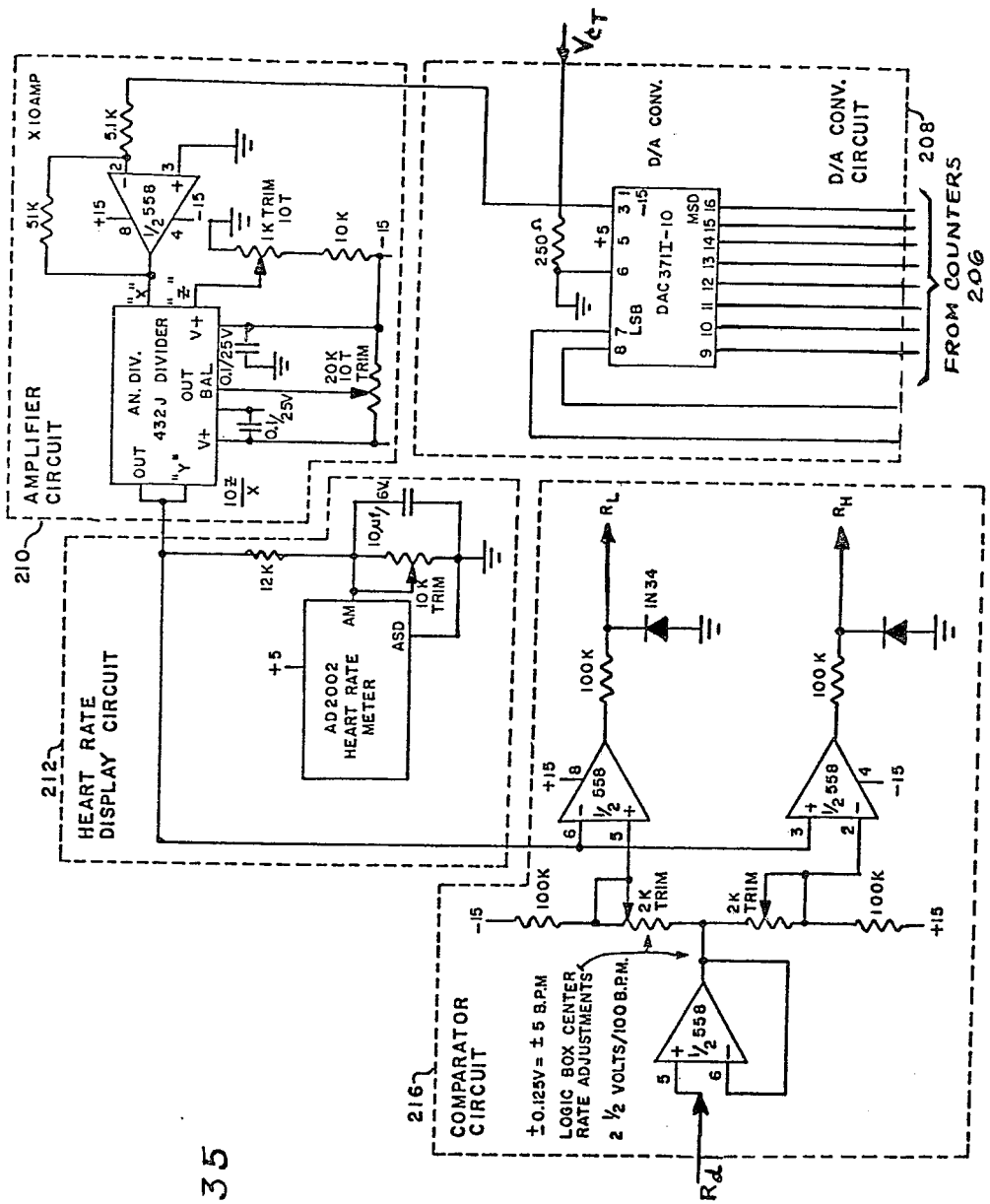

In view of the fact that the detailed circuit diagrams in FIGS. 24–25 comprise only conventional gates, flip-flops, counters, etc., and in view of the above detailed functional description of these circuits, FIGS. 24–35 are believed to be self-explanatory to those skilled in the art.

It will be appreciated by those skilled in the art that although the invention has been described in terms of an exemplary embodiment, modifications and variations can be effected in this embodiment without departing from the scope and spirit of the invention. For example, the pump system may be run so as to maintain constant the patient's systolic pressure SP, in which case the patient's diastolic pressure DP and heart rate HR are used as inputs to an appropriate logic circuit. Similarly, a predetermined heart rate HR may be maintained, in which case the patient's diastolic and systolic pressures are used as inputs to another suitable logic box. In either case, the control circuitry peripheral to the logic box 510 would of course also be appropriately modified. Other combinations and permutations of physiologic control and independently controlled pump parameters may also be used as should now be appreciated.

What is claimed is:

1. A pulsatile fluid pumping system for circulating blood or blood-like fluids within the vascular systems of living tissue under automatically controlled and predetermined plural physiologic parameters, said system comprising:
   a pulsatile pump adapted for connection to said living tissue and having plural pumping parameters which may be independently controlled during cyclic operation of the pump, and
   sensing and control means for simultaneously monitoring plural predetermined physiologic parameters of said living tissue and for simultaneously controlling the plural independent pumping parameters as a predetermined logical function of said plural physiologic parameters so as to substantially maintain all such physiologic parameters at respectively corresponding predetermined values.

2. A pulsatile fluid pumping system as in claim 1 wherein said sensing and control means includes means for monitoring physiologic parameters including the systolic pressure, diastolic pressure and repetition rate of a blood pressure waveform produced in the vascular system of said living tissue.

3. A pulsatile fluid pumping system as in claim 1 or 2 wherein said pulsatile pump includes means permitting control of independent pumping parameters including the driving speed, stroke length and repetition rate of a reciprocating piston.

4. A pulsatile fluid pumping system as in claim 1 wherein:
   said sensing and control means includes means for monitoring physiologic parameters including the systolic pressure (SP), the diastolic pressure (DP) and repetition rate (HR) of a blood pressure waveform produced in the vascular system of said living tissue;
   said pulsatile pump includes means permitting control of independent pumping parameters including the delivery time (PDT) required for the pump to eject a certain delivery volume (PDV) of fluid;
   said pump being controlled by said sensing and control means to begin a new cycle of operation each time a predetermined desired DP level is sensed and to alter PDT and PDV parameters as set forth in the following logical function table to maintain SP and HR parameters at predetermined desired values:

|  | to increase SP | SP satisfactory | to decrease SP |
| --- | --- | --- | --- |
| to increase HR | decrease PDT | decrease PDT decrease PDV | decrease PDV |
| HR satisfactory | decrease PDT increase PDV | no change | increase PDT decrease PDV |
| to decrease HR | increase PDV | increase PDT increase PDV | increase PDT |

5. An extracorporeal pulsatile fluid pumping system for circulating blood or blood-like fluids within living tissue under automatically controlled and predetermined plural physiologic parameters, said system comprising:
   a cyclically operated pulsatile fluid pump which, when supplied with a fluid, operates at a controllable pump delivery speed (PDS) to deliver to said living tissue a controllable pump delivery volume (PDV) of fluid in a pump cycle time (PCT) period;
   at least one sensor and feedback circuit adapted to monitor a plurality of predetermined physiologic parameters within said living tissue and to provide a respectively corresponding plurality of first electrical signals representing the actual instantaneous values of such parameters in the living tissue;
   a plurality of manually adjustable input controls which provide a plurality of second electrical signals each representing the desired value for a respectively corresponding one of said predetermined physiologic parameters; and
   control circuits connected to receive said first and second electrical signals, to compare said actual instantaneous values with the respectively corresponding desired values and to control two or more of the pump parameters PDS, PDV and PCT as a predetermined function of said comparison so as to correct for detected deviations of the actual values from the desired values.

6. A pulsatile fluid pumping system as in claim 5 wherein the control circuits include means adapted to control two or more of the PDS, PDV and PCT pump parameters as a function of detected changes in one or more of the physiologic parameters of systolic fluid pressure (SP) diastolic fluid pressure (DP) and pressure wave repetition period or heart period (HP) in accordance with the following tabulation where " ↑ " represents "increase," " ↓ " represents "decrease," and "—" represents "no change":

| Detected deviation of SP, DP and/or HP from desired normal values | | | Possible controlled change in PDS, PDV and/or PCT to correct for detected physiological deviation | | |
| --- | --- | --- | --- | --- | --- |
| SP | DP | HR(1/HP) | PDS | PDV | PCT |
| ↑ | = | ↑ | ↓ | — | = |
| ↓ | = | ↓ | ↑ | — | = |
| ↑ | = | ↓ | — | ↓ | = |
| ↓ | = | ↑ | — | ↑ | = |
| ↑ | = | — | ↓ | ↓ | = |
| ↓ | = | — | ↑ | ↑ | = |
| — | = | ↑ | ↓ | ↑ | = |
| — | = | ↓ | ↑ | ↓ | = |
| ↑ | ↓ | = | ↑ | — | = |
| ↑ | ↑ | = | — | ↓ | = |
| ↓ | ↓ | = | — | ↑ | = |
| ↑ | — | = | ↓ | ↑ | = |
| ↓ | — | = | ↑ | ↑ | = |
| — | ↓ | = | ↑ | ↑ | = |
| — | ↑ | = | ↑ | ↓ | = |

7. A pulsatile fluid pumping system as in claim 5 wherein said sensor and feedback circuit includes means for monitoring said plurality of physiologic parameters including at least two of the systolic blood pressure, diastolic blood pressure and heart period parameters.

8. A pulsatile fluid pumping system as in any of claims 1, 2, 4, 5, 6 or 7 including visual display means connected to monitor and display visual indications related to said plurality of predetermined physiologic parameters.

9. In a pulsatile fluid pumping system for circulating blood or blood-like fluids within the vascular system of living tissue, the improvement comprising:
sensor means for sensing plural predetermined physiologic parameters within said living tissue;
input means for presenting a predetermined desired value for each of said plural physiologic parameters;
comparing means connected for comparing each of the sensed plural physiologic parameter values with its respectively corresponding predetermined desired value and providing corresponding plural output signals respectively representing detected deviations therefrom; and
control means connected for controlling plural independent pumping parameters of said pumping system in response to a predetermined logical function of said detected deviations.

10. An improvement as in claim 9 wherein said sensor means includes means for monitoring physiologic parameters including the systolic pressure, diastolic pressure and repetition rate of a blood pressure waveform produced in the vascular system of said living tissue.

11. An improvement as in claims 9 or 10 wherein said pumping system includes means permitting control of independent pumping parameters including the driving speed, stroke length and repetition rates of a reciprocating piston.

12. An improvement as in claim 9 wherein:
said sensor means includes means for monitoring physiologic parameters including the systolic pressure (SP), the diastolic pressure (DP) and repetition rate (HR) of a blood pressure waveform produced in the vascular system of said living tissue;
said pumping system includes means permitting control of independent pumping parameters including the delivery time (PDT) required for the pumping system to eject a certain delivery volume (PDV) of fluid;
said pumping system being controlled by said control means to begin a new cycle of operation each time a predetermined desired DP level is sensed and to alter PDT and PDV parameters as set forth in the following logical function table to maintain SP and HR parameters at predetermined desired values:

| | to increase SP | SP satisfactory | to decrease SP |
| --- | --- | --- | --- |
| to increase HR | decrease PDT | decrease PDT decrease PDV | decrease PDV |
| HR satisfactory | decrease PDT increase PDV | no change | increase PDT decrease PDV |
| to decrease HR | increase PDV | increase PDT increase PDV | increase PDT |

13. A method for pulsatile circulation of blood or blood-like fluids within the vascular systems of living tissue under automatically controlled and predetermined plural physiologic parameters, said method comprising the steps of:
simultaneously monitoring plural predetermined physiologic parameters of said living tissue; and
simultaneously controlling plural independent pumping parameters of a pulsatile fluid pumping system as a predetermined logical function of said plural physiologic parameters so as to substantially maintain all such physiologic parameters at respectively corresponding predetermined values.

14. A method as in claim 13 wherein said physiologic parameters comprise the systolic pressure, diastolic pressure and repetition rate of a blood pressure waveform produced in the vascular system of said living tissue.

15. A method as in claim 13 or 14 wherein said independent pumping parameters comprise the driving speed, stroke length and repetition rate of a reciprocating piston.

16. A method as in claim 13 wherein:
said physiologic parameters comprise the systolic pressure (SP), the diastolic pressure (DP) and repetition rate (HR) of a blood pressure waveform produced in the vascular system of said living tissue;
said independent pumping parameters comprise the delivery time (PDT) required for the pump to eject a certain delivery volume (PDV) of fluid;
said pump being controlled to begin a new cycle of operation each time a predetermined desired DP level is sensed and to alter PDT and PDV parameters as set forth in the following logical function table to maintain SP and HR parameters at predetermined desired values:

|  | to increase SP | SP satisfactory | to decrease SP |
|---|---|---|---|
| to increase HR | decrease PDT | decrease PDT decrease PDV | decrease PDV |
| HR satisfactory | decrease PDT increase PDV | no change | increase PDT decrease PDV |
| to decrease HR | increase PDV | increase PDT increase PDV | increase PDT |

17. A method for pulsatile circulation of blood or blood-like fluids within living tissue under automatically controlled and predetermined plural physiologic parameters, said method comprising the steps of:
operating a cyclical pulsatile fluid pump at a controllable pump delivery speed (PDS) to deliver to said living tissue a controllable pump delivery volume (PDV) of fluid in a pump cycle time (PDC) period;
monitoring a plurality of predetermined physiologic parameters within said living tissue and generating a respectively corresponding plurality of first electrical signals representing the actual instantaneous values of such parameters in the living tissue;
manually controlling and providing a plurality of second electrical signals each representing the desired value for a respectively corresponding one of said predetermined physiologic parameters; and
comparing said actual instantaneous values with the respectively corresponding desired values and controlling two or more of the pump parameters PDS, PDV and PCT as a predetermined function of said comparison so as to correct for detected deviations of the actual values from the desired values.

18. A method as in claim 17 wherein two or more of the PDS, PDV and PCT pump parameters are controlled as a function of detected changes in one or more of the physiologic parameters of systolic fluid pressure (SP) diastolic fluid pressure (DP) and pressure wave repetition period or heart period (HP) in accordance with the following tabulation where "↑" represents "increase," "↓" represents "decrease," and "—" represents "no change".

| Detected deviation of SP, DP and/or HP from desired normal values | | | Possible controlled change in PDS, PDV and/or PCT to correct for detected physiological deviation | | |
|---|---|---|---|---|---|
| SP | DP | HR(1/HP) | PDS | PDV | PCT |
| ↑ | = | ↑ | ↓ | — | = |
| ↓ | = | ↓ | ↑ | — | = |
| ↑ | = | ↓ | — | ↓ | = |
| ↓ | = | ↑ | — | ↑ | = |
| ↑ | = | = | — | ↓ | = |
| ↓ | = | = | — | ↑ | = |
| — | = | ↑ | ↓ | ↑ | = |
| — | = | ↓ | ↑ | ↓ | = |
| ↑ | ↓ | = | ↓ | — | = |
| ↓ | ↑ | = | ↑ | — | = |
| ↑ | ↑ | = | — | ↓ | = |
| ↓ | ↓ | = | — | ↑ | = |
| ↑ | — | = | ↓ | ↓ | = |
| ↓ | — | = | ↑ | ↑ | = |

| Detected deviation of SP, DP and/or HP from desired normal values | | | Possible controlled change in PDS, PDV and/or PCT to correct for detected physiological deviation | | |
|---|---|---|---|---|---|
| SP | DP | HR(1/HP) | PDS | PDV | PCT |
| — | ↓ | = | ↓ | ↑ | = |
| — | ↑ | = | ↑ | ↓ | = |

19. A method as in claim 17 wherein said plurality of physiologic parameters include at least two of the systolic blood pressure, diastolic blood pressure and heart period parameters.

20. A method as in any of claims 13, 14, 16, 17, 18 or 19 including the steps of monitoring and visually displaying said plurality of predetermined physiologic parameters.

21. An improved method for pulsatile circulation of blood or blood-like fluids within the vascular system of living tissue, said improved method comprising:
sensing plural predetermined physiologic parameters within said living tissue;
manually providing a predetermined desired value for each of said plural physiologic parameters;
comparing each of the sensed plural physiologic parameter values with its respectively corresponding predetermined desired value and providing corresponding plural output signals respectively representing detected deviations therefrom; and
controlling plural independent pumping parameters of said pumping system in response to a predetermined logical function of said detected deviations.

22. An improved method as in claim 21 wherein said physiologic parameters comprise the systolic pressure, diastolic pressure and repetition rate of a blood pressure waveform produced in the vascular system of said living tissue.

23. An improved method as in claims 21 or 22 wherein said independent pumping parameters comprise the driving speed, stroke length and repetition rates of a reciprocating piston.

24. An improved method as in claim 21 wherein:
said physiologic parameters comprise the systolic pressure (SP), the diastolic pressure (DP) and repetition rate (HR) of a blood pressure waveform produced in the vascular system of said living tissue;
said independent pumping parameters comprise the delivery time (PDT) required for the pumping system to eject a certain delivery volume (PDV) of fluid;
said pumping system being controlled to begin a new cycle of operation each time a predetermined desired DP level is sensed and to alter PDT and PDV parameters as set forth in the following logical function table to maintain SP and HR parameters at predetermined desired values:

|  | to increase SP | SP satisfactory | to decrease SP |
|---|---|---|---|
| to increase HR | decrease PDT | decrease PDT decrease PDV | decrease PDV |
| HR satisfactory | decrease PDT increase PDV | no change | increase PDT decrease PDV |
| to decrease HR | increase PDV | increase PDT increase PDV | increase PDT |

* * * * *